US007291724B2

(12) United States Patent
Stüber et al.

(10) Patent No.: US 7,291,724 B2
(45) Date of Patent: Nov. 6, 2007

(54) OLIGONUCLEOTIDES FOR RAPIDLY IDENTIFYING MICROBIAL DNA OR RNA

(75) Inventors: Frank Stüber, Bonn (DE); Andreas Hoeft, Bonn (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 11/592,085

(22) Filed: Nov. 2, 2006

(65) Prior Publication Data
US 2007/0042422 A1    Feb. 22, 2007

Related U.S. Application Data

(63) Continuation of application No. 10/168,639, filed as application No. PCT/DE00/04610 on Dec. 27, 2000, now Pat. No. 7,169,555.

(30) Foreign Application Priority Data
Dec. 23, 1999  (DE) ................. 199 62 895
May 31, 2000  (DE) ................. 100 27 113

(51) Int. Cl.
*C07H 21/04* (2006.01)
*C12Q 1/68* (2006.01)
*C12P 19/34* (2006.01)
*G01N 33/00* (2006.01)

(52) U.S. Cl. ................ 536/24.32; 536/24.33; 435/6; 435/91.1; 435/91.2; 436/94

(58) Field of Classification Search ............ 435/6, 435/91.1, 91.2, 183, 810; 436/94; 536/23.1, 536/24.3, 24.32, 24.33
See application file for complete search history.

(56) References Cited

U.S. PATENT DOCUMENTS

| | | | |
|---|---|---|---|
| 5,605,796 A | 2/1997 | Chen et al. | |
| 5,654,418 A | 8/1997 | Sheiness et al. | |
| 5,776,694 A | 7/1998 | Sheiness et al. | |
| 5,846,772 A | 12/1998 | Hodgson et al. | |
| 6,174,670 B1 | 1/2001 | Wittwer et al. | |
| 6,326,145 B1 | 12/2001 | Whitcombe et al. | |
| 6,635,427 B2 * | 10/2003 | Wittwer et al. ......... | 435/6 |

FOREIGN PATENT DOCUMENTS

| | | |
|---|---|---|
| WO | WO 95/13396 A2 | 5/1995 |
| WO | WO 97/07238 | 2/1997 |
| WO | WO 00/66777 | 11/2000 |

OTHER PUBLICATIONS

Jensen et al., "Rapid Identificaiton of bacteria on the basis of polymease chain reaction-amplified ribosomal DNA spacer polymorphisms," Applied and Envronmental Microbiology 1993 59(4), pp. 945-952.*

Ririe et al., "Product Differentiation by Analysis of DNA Melting Curves during the Polymerase Chain Reaction", *Analytical Biochemistry*, 1997, pp. 154-160.
Nauck et al., "Rapid, Homogeneous Genotyping of the 4G/5G Polymorphism in the Promoter Region of the PAII Gene by Fluorescence Resonance Energy Transfer and Probe Melting Curves", *Clinical Chemistry*, vol. 45, No. 8, Aug. 1, 1999, pp. 1141-1147.
Von Ahsen et al., "Application of a Thermodynamic Nearest-Neighbor Model to Estimate Nucleic Acid Stability and Optimize Probe Design: Prediction of Melting Points of Multiple Mutations of Apolipoprotein B-3500 and Factor V with a Hybridization Probe Genotyping Assay on the LightCycler", *Clinical Chemistry*, Bd. 45, No. 12, Dec. 1, 1999, pp. 2094-2101.
De Silva, "Rapid Genotyping and Quantification on the LightCycler with Hybridization Probes", *Biochemica*, No. 2, 1998, pp. 12-15.
Shepherd et al., "Monitoring of Fluorescence during DNA Melting as a Method for Discrimination and Detection of PCR Products in Variety Identification", *Molecular Breeding*, vol. 4, No. 6, 1998, pp. 509-517.
Woo et al., "Identification of *Leptospira biflexa* by Real-Time Homogeneous Detection of Rapid Cycle PCR Product", *Journal of Microbiological Methods*, vol. 35, No. 1, Feb. 1999, pp. 23-30.
Klausegger et al., "Gram Type-Specific Broad Range PCR Amplification for Rapid Detection of 62 Pathogenic Bacteria", *Journal of Clinical Microbiology*, vol. 37, No. 2, Feb. 1999, pp. 464-466.
Anthony et al., "Rapid Diagnosis of Bacteremia by Universal Amplification of 23S Ribosomal DNA Followed by Hybridization to an Oligonucleotide Array", *Journal of Clinical Microbiology*, vol. 38, No. 2, Feb. 2000, pp. 781-788.
Bernard et al., "Homogeneous Multiplex Genotyping of Hemochromatosis Mutations with Fluorescent Hybridization Probes", *American Journal of Pathology*, vol. 153, No. 4, Oct. 1998, pp. 1055-1061.
Katalog der Firma Boehringer Mannheim von 1996, Extrakt, "Kits for DNA and RNA Amplification".
Katalog der Firma Gibco BRL von 1996, Seiten (pp. 115-116, "Cloning", Life Technologies.
Jensen, M.A., Webster, J.A. and Straus, N., "Rapid Identification of Bacteria on the Basis of Polymerase Chain Reaction-Amplified Ribosomal DNA Spacer Polymorphisms", 59 (4) *App. and Environmental Microbiology*, 1993, pp. 945-952 (abstract).
Epsy et al., "Diagnosis of Herpes Simplex Virus Infections in the Clinical Laboratory by LighCycler PCR", *Journal of Clinical Microbiology*, vol. 38, No. 2, Feb. 2000, pp. 795-799.
Pietila et al., "Rapid Differentiation of *Borrelia garinii* from *Borrelia afzelii* and *Borrelia burgdorferi* Sensu Stricto by LightCycler Fluorescence Melting Curve Analysis of a PCR Product of the recA Gene", *Journal of Clinical Microbiology*, vol. 38, No. 7, Jul. 2000, pp. 2756-2759.
Database EMBL [Online] Oct. 11, 1997, "Sequence 53 from patent US 5,654,418."XP-002429034, EBI accession No. EMBL: I59998, Database accession No. I59998.
Database EMBL [Online] Mar. 7, 1997, "Sequence 4 from Patent WO 95/13396." XP-002429035, EBI accession No. EMBL: A44457, Database accession No. A44457.

* cited by examiner

*Primary Examiner*—Bradley L. Sisson
(74) *Attorney, Agent, or Firm*—Frishauf, Holtz, Goodman & Chick, P.C.

(57) ABSTRACT

An oligonucoeotide selected from the group consisting of ISN2 (SEQ ID NO: 43), ISN2* (SEQ ID NO: 44), ISN (SEQ ID NO: 34), ISP2 (SEQ ID NO: 46), ISP2* (SEQ ID NO: 45) and ISP (SEQ ID NO: 33).

7 Claims, 17 Drawing Sheets

FIG.1
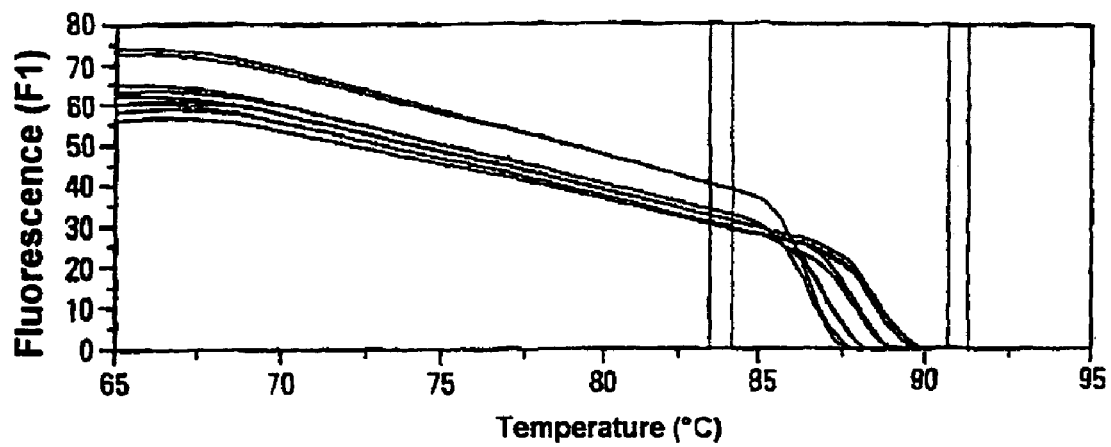
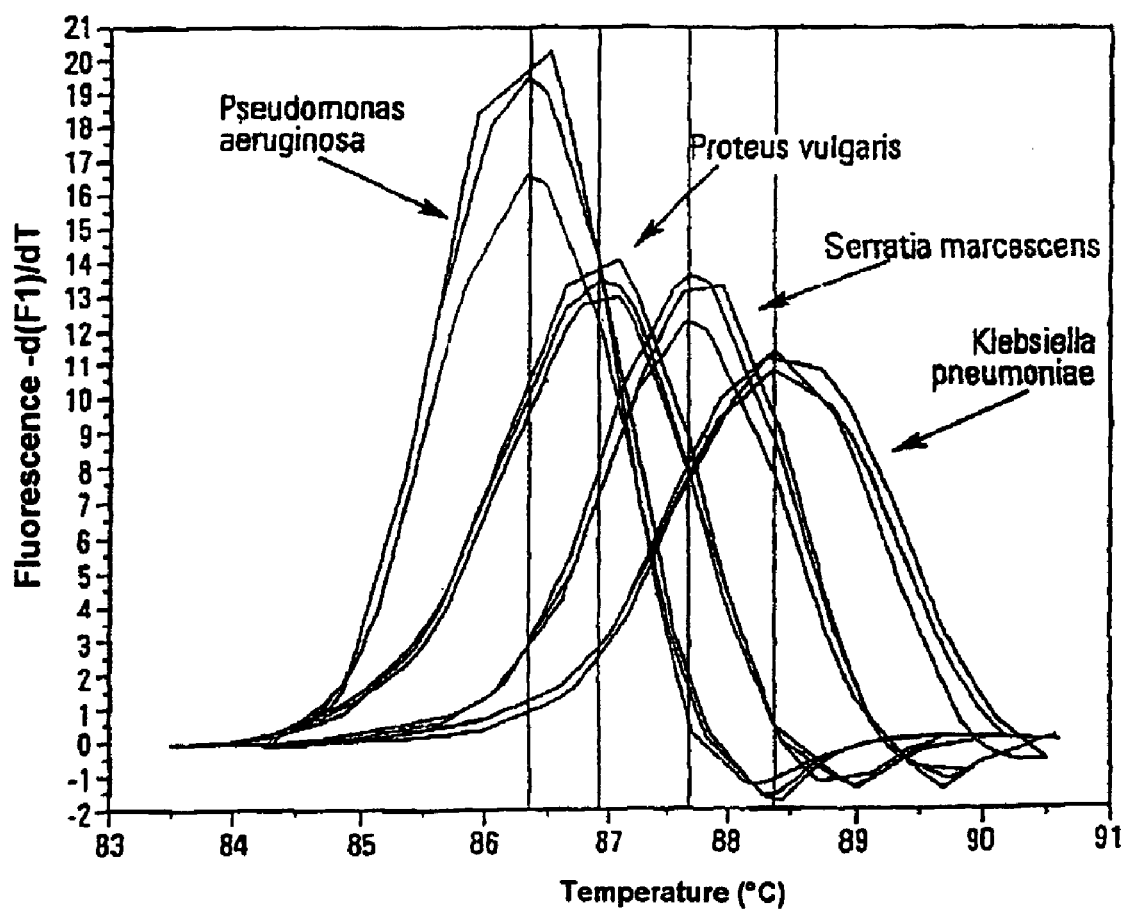

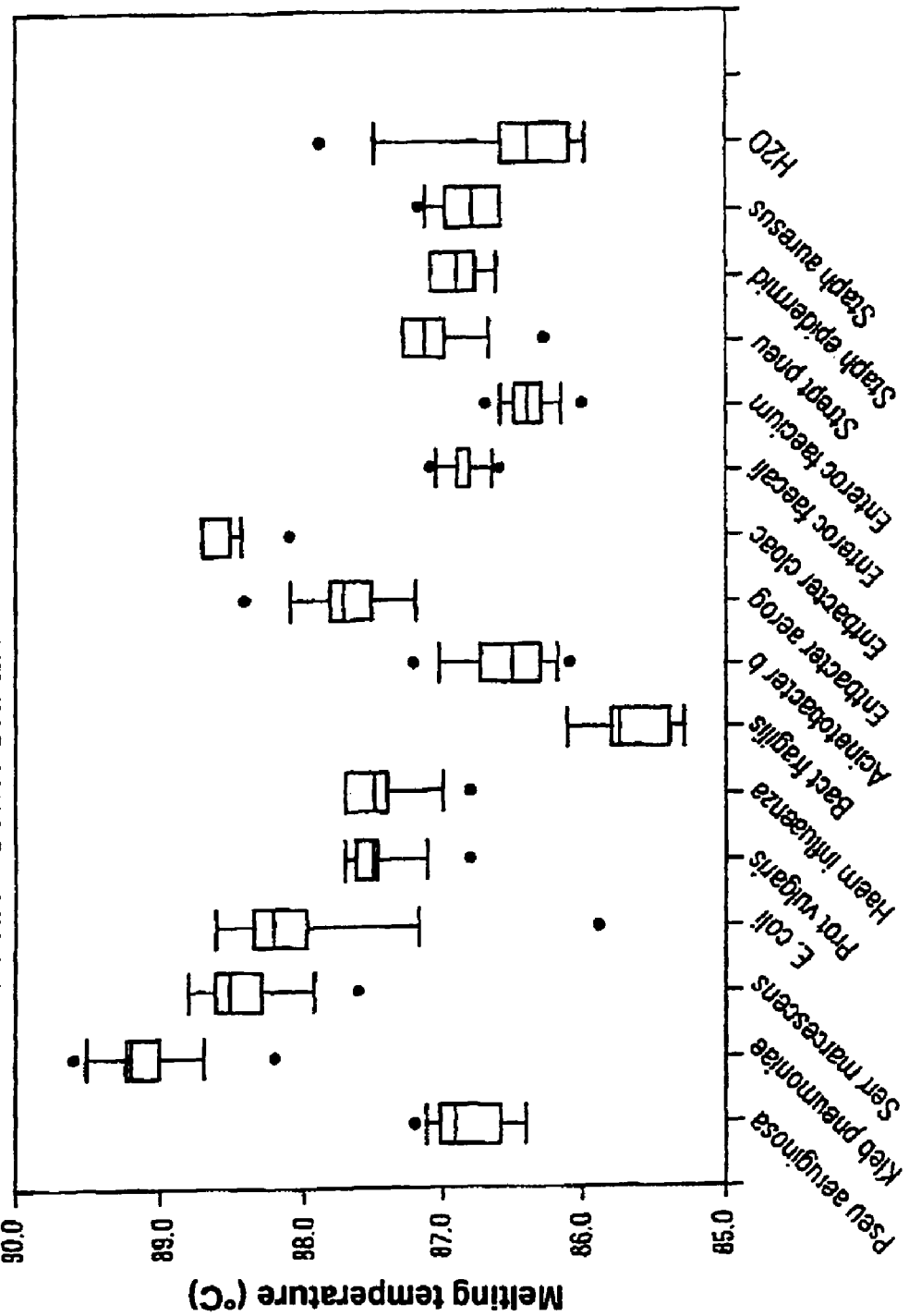
FIG. 1a Melting points of relevant organisms (PLK1/2) dsDNA + SYBR-GREEN

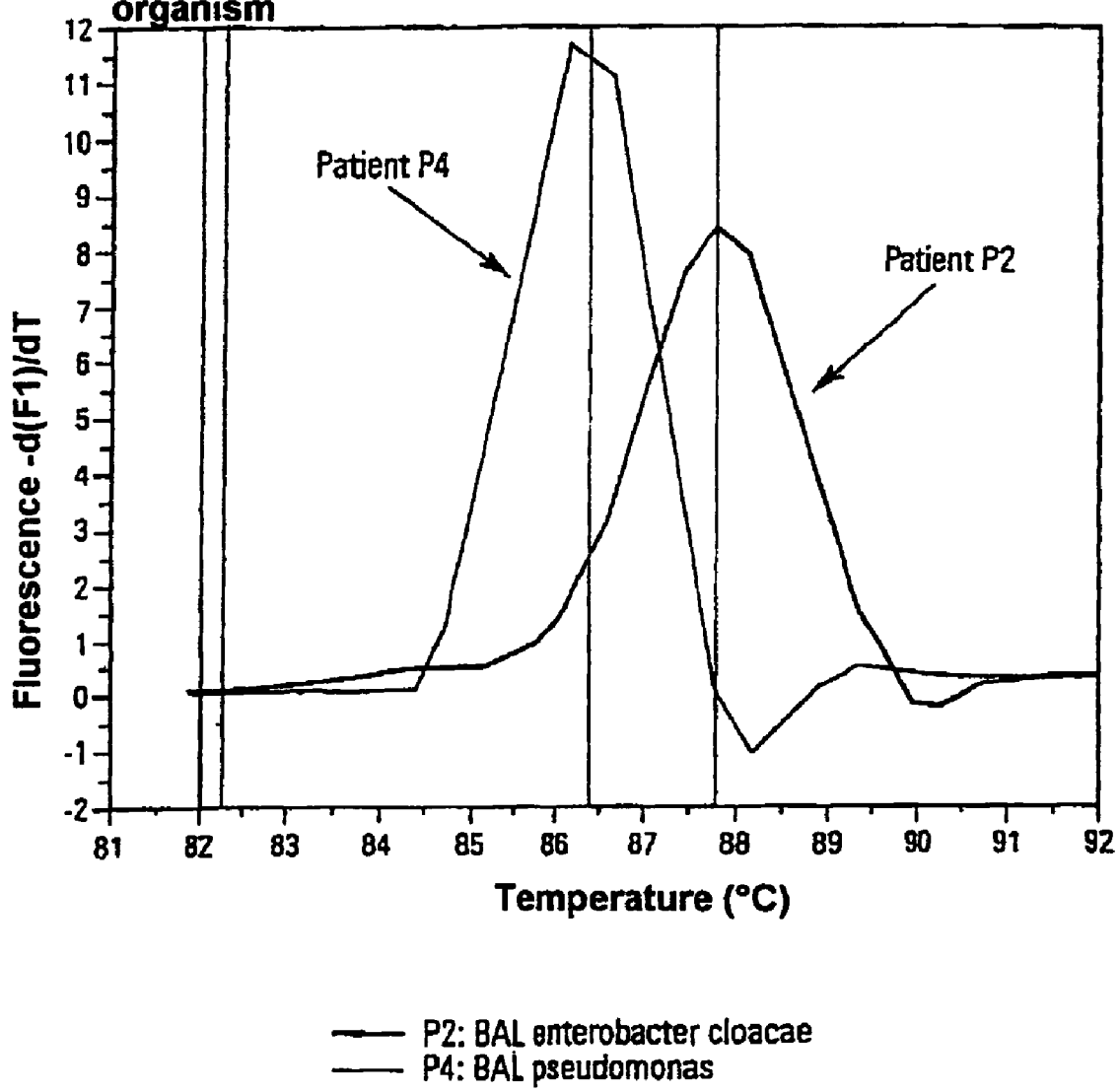

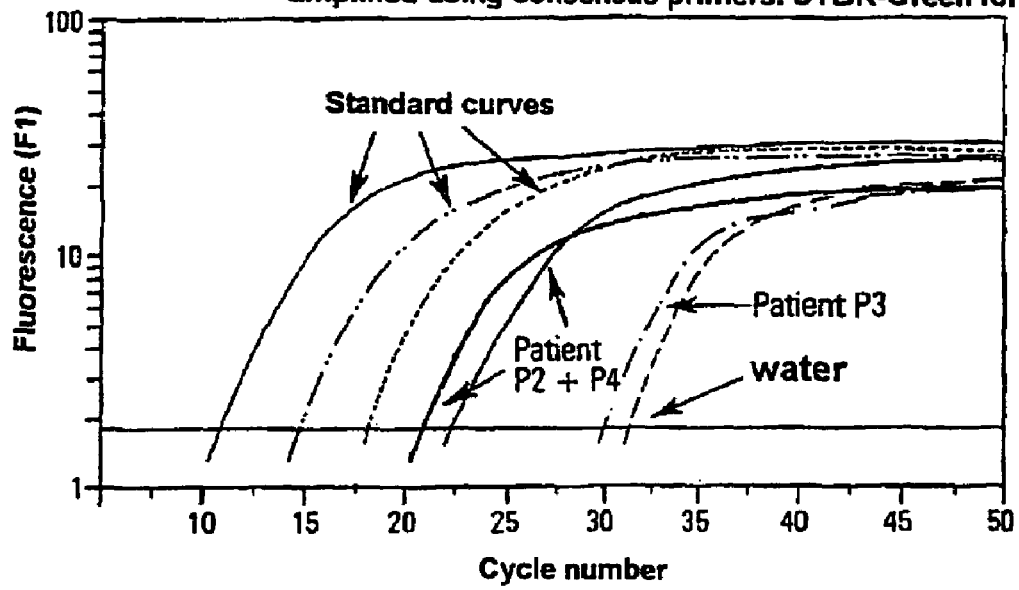
FIG.1c BAL from patients. Diluted 1 : 10 after preparation and amplified using consensus primers. SYBR-Green format
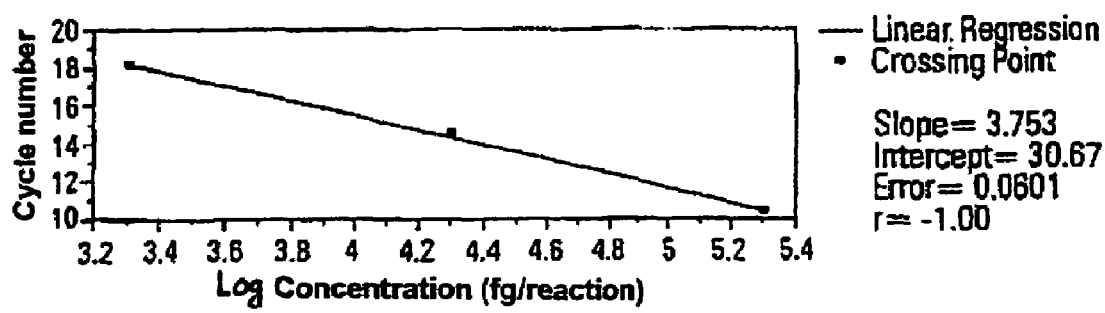
— Linear Regression
• Crossing Point
Slope= 3.753
Intercept= 30.67
Error= 0.0601
r= -1.00
| | | | |
|---|---|---|---|
| —— | 7 P2BAL 1:10 | 436.8 | 20.76 |
| —·— | 8 P3BAL 1:10 | 1.365 | 30.16 |
| —— | 9 P4BAL 1:10 | 141.6 | 22.60 |
| — — | 16 H2O | 0.663 | 31.34 |

FIG.2
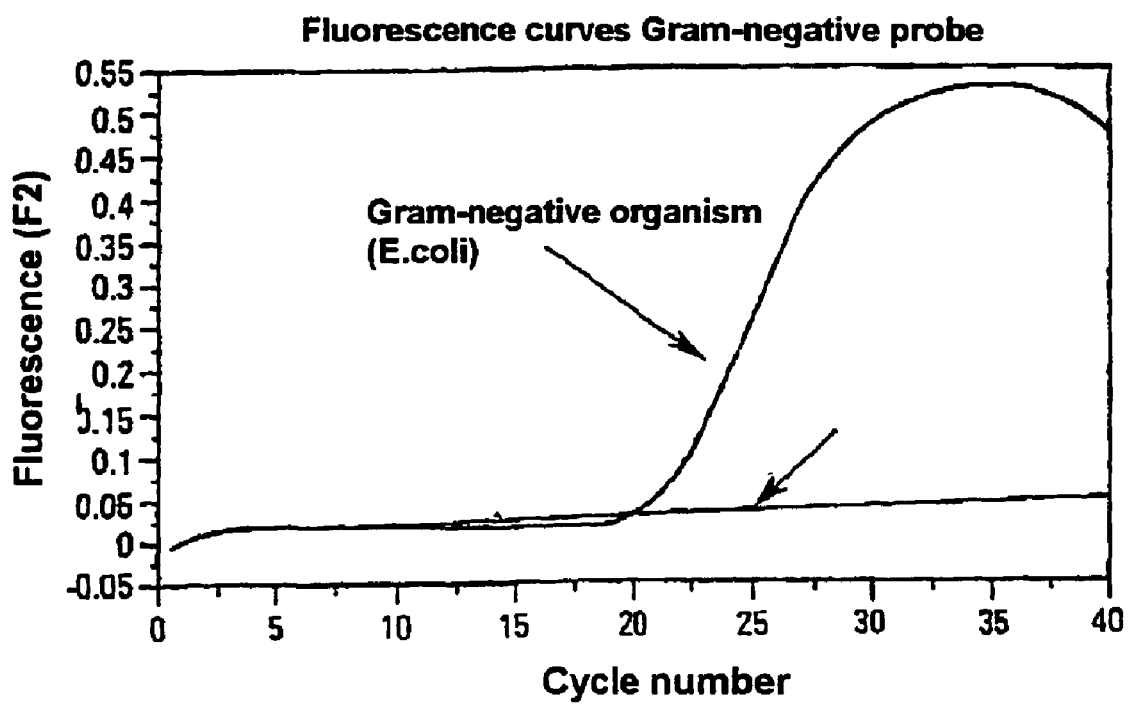
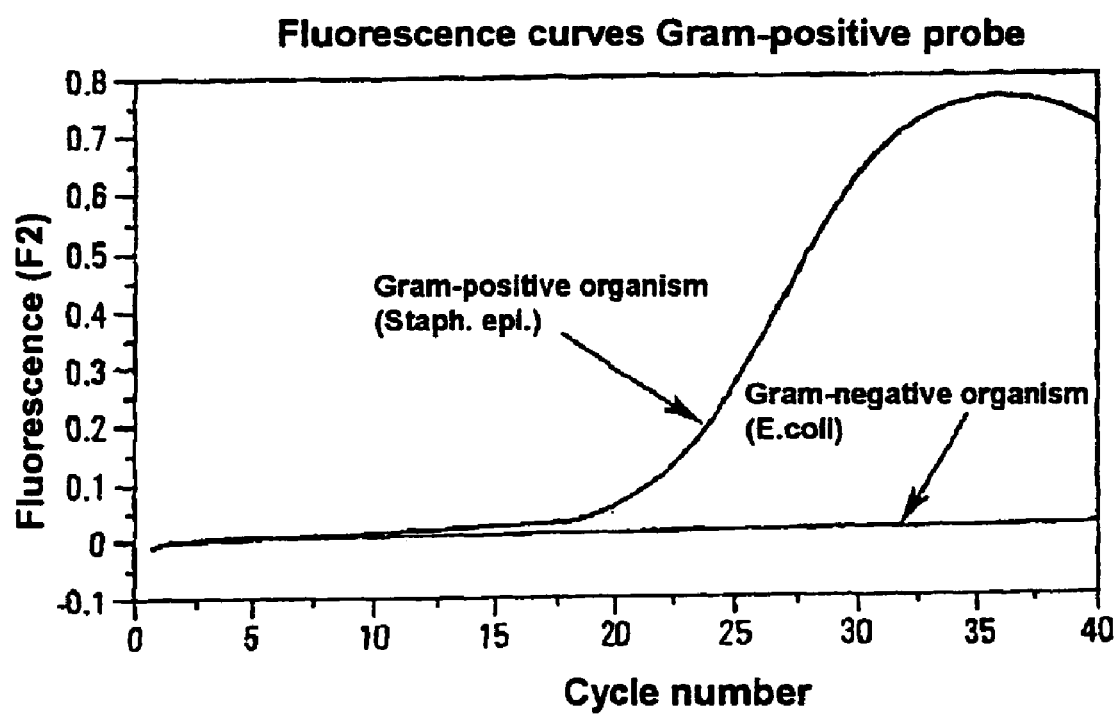

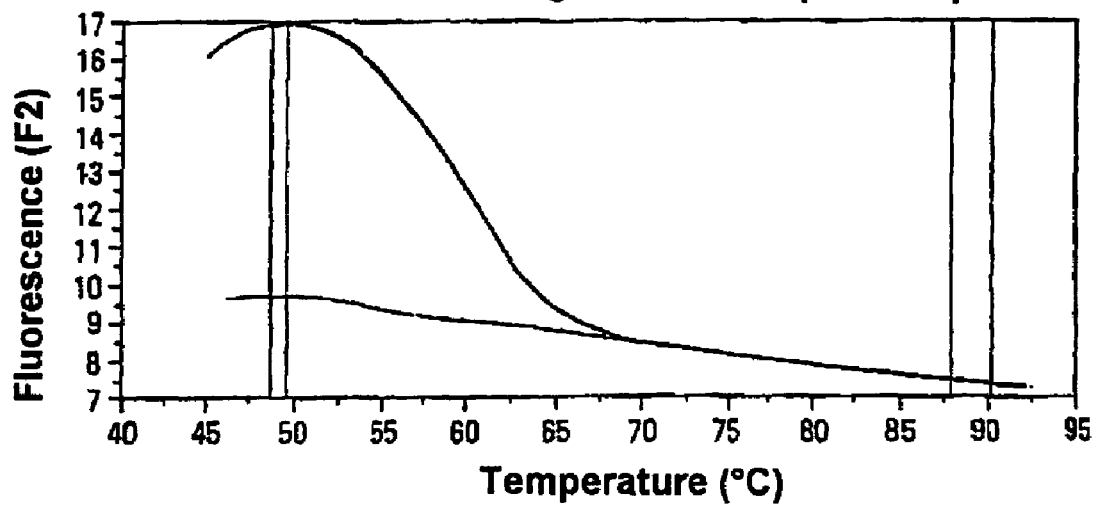
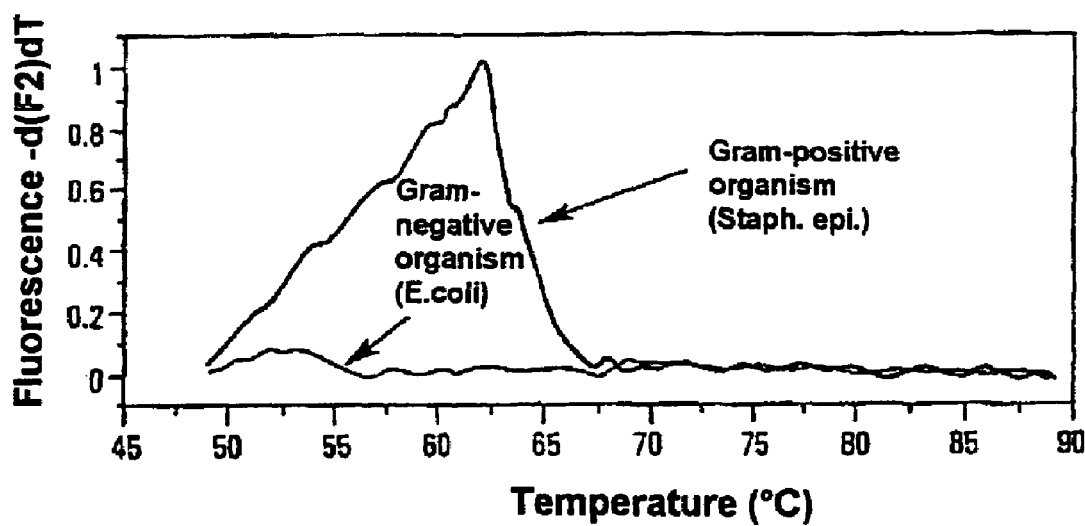
FIG. 3 Melting curve Gram-positive probe

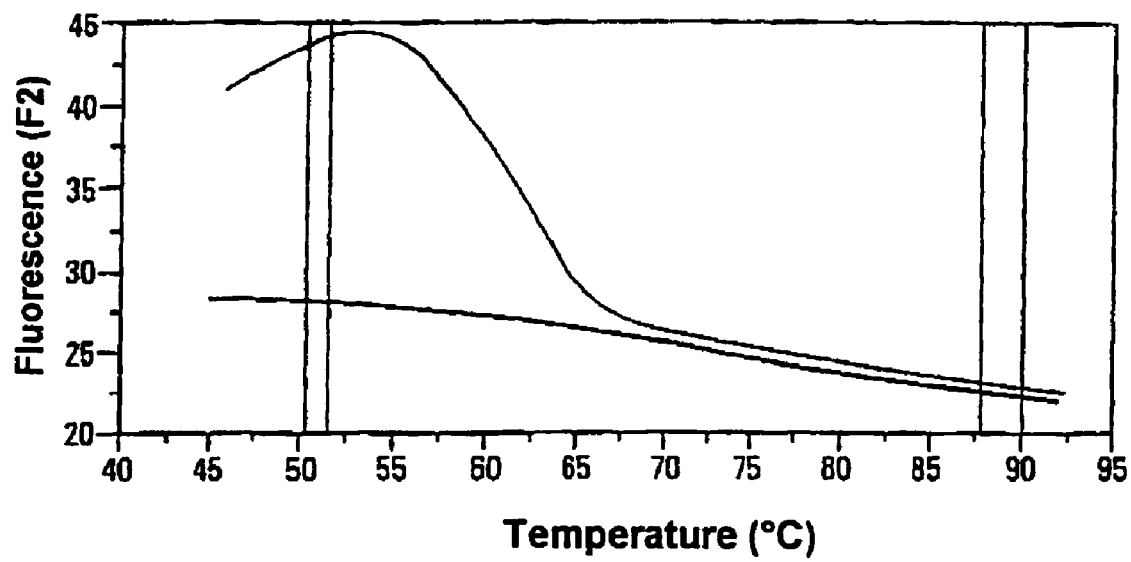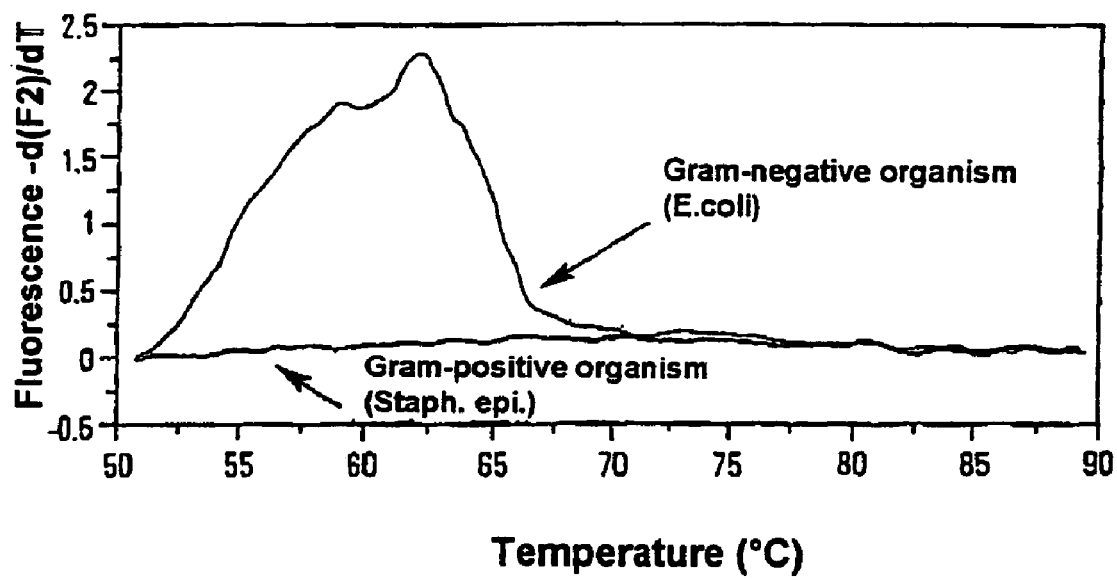
FIG.4 Melting curve Gram-negative probe

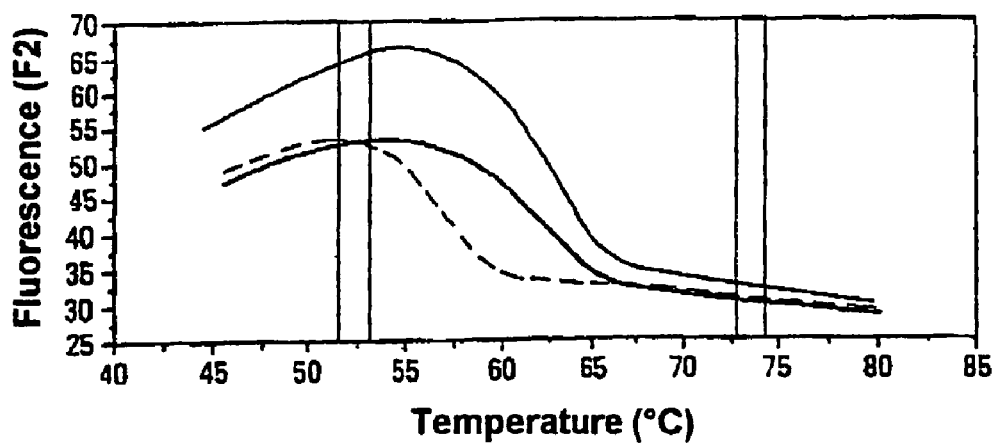
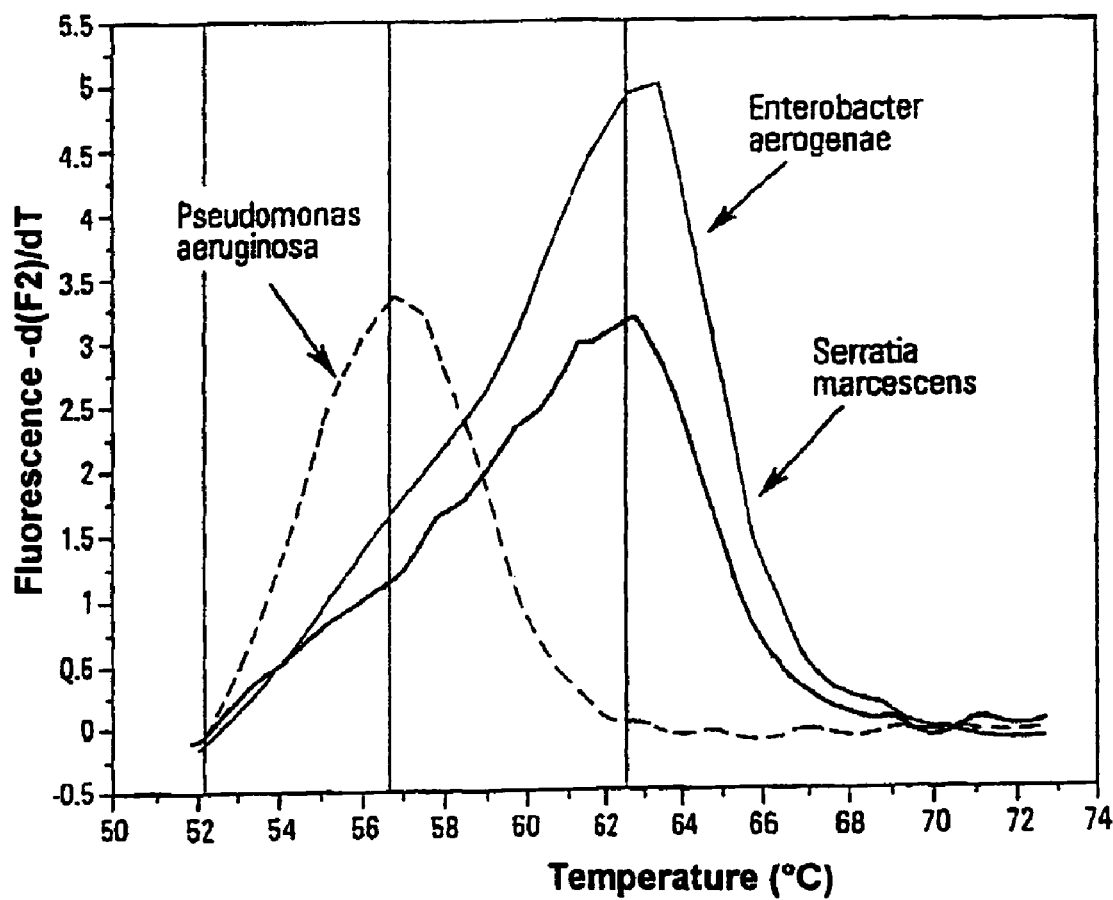
FIG. 5 Melting curves using a Gram-negative probe:

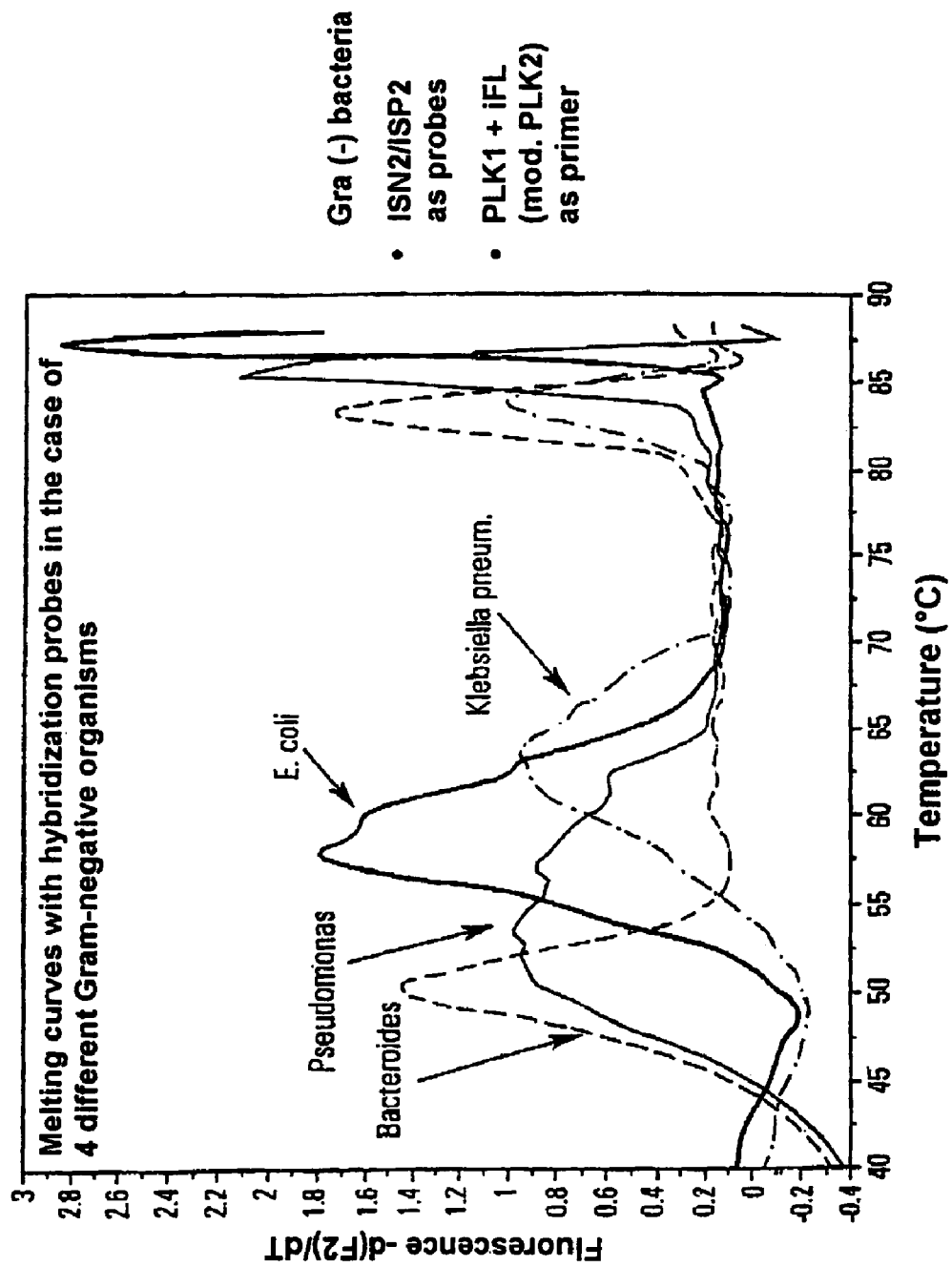

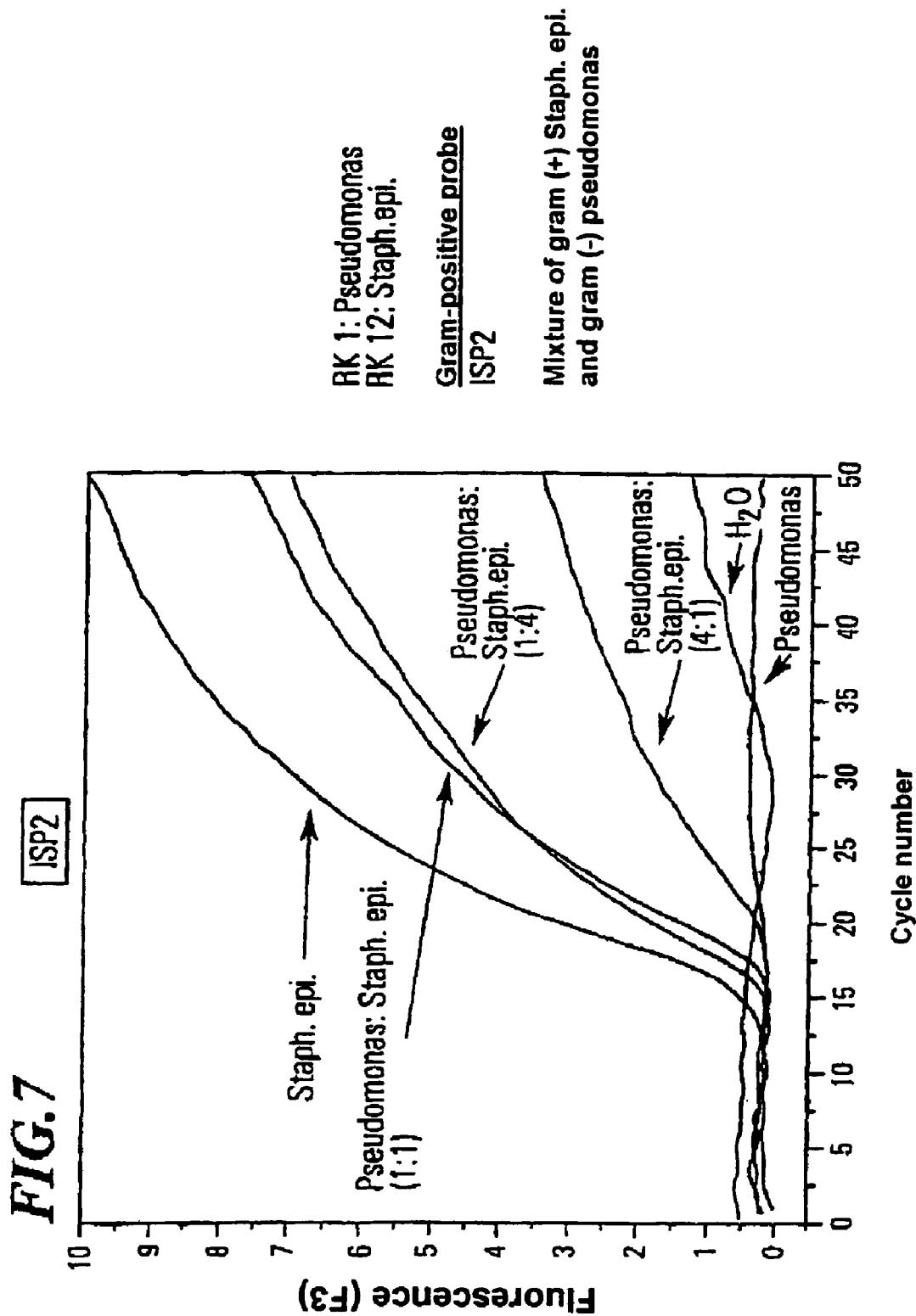

```
PSEUDAER:          AGACACGGTCCAGACTCCT ACGGGAGGCAGCAGTGGGGAATATTGGACAA 388
ACINBAUMANII:      AGACACGGCCCAGACTCCT ACGGGAGGCAGCAGTGGGGAATATTGGACAA 337
LEGPNEU:           AGACACGGTCCAGACTCCT ACGGGAGGCAGCAGTGGGGAATATTGGACAA 348
SERMAR:            AGACACGGTCCAGACTCCT ACGGGAGGCAGCAGTGGGGAATATTGCACAA 375
ENTEROBACTAEROG:   AGACACGGTCCAGACTCCT ACGGGAGGCAGCAGTGGGGAATATTGCACAA 340
KLEBSPNEU:         AGACACGGTCCAGACTCCT ACGGGAGGCAGCAGTGGGGAATATTGCACAA 365
ENTEROBACTCLOAC:   AGACACGGTCCAGACTCCT ACGGGAGGCAGCAGTGGGGAATATTGCACAA 345
ECOLI:             AGACACGGTCCAGACTCCT ACGGGAGGCAGCAGTGGGGAATATTGCACAA 373
PROTVULG:          AGACACGGCCCAGACTCCT ACGGGAGGCAGCAGTGGGCAATATTGCACAA 373
HEMOINFLU:         AGACACGGTCCAGACTCCT ACGGGAGGCAGCAGTGGGGAATATTGCGCNA 374
MYCOBTUBERC:       AGATACGGCCCAGACTCCT ACGGGAGGCAGCAGTGGGGAATATTGCACAA 363
CORYNEYJEIJ:       AGACACGGCCCAGACTC-T ACGGGAGGCAGCAGTGGG-AATATTGCACAA 359
ENTEROCOCFAECALI:  AGACACGGCCCAGACTCCT ACGGGAGGCAGCAGTAGGGAATCTTCGGCAA 344
ENTEROCOCFAECIUM:  AGACACGGCCCAAACTCCT ACGGGAGGCAGCAGTAGGGAATCTTCGGCAA 344
STREPTPYOGEN:      AGACACGGCCCNGACTCCT ACGGGAGGCAGCNGTAGGGAATCTTCGGCNA 278
STAPHEPI:          AGACACGGTCCAGACTCCT ACGGGAGGCAGCAGTAGGGAATCTTCCGCAA 354
STAPHAUREUS:       AGACACGGTCCAGACTCCT ACGGGAGGCAGCAGTAGGGAATCTTCCGCAA 368
MYCOBACTPNEUM:     AGACACGGCCCATACTCCT ACGGGAGNCAGCAGTAGGGAATTTTTCACAA 371
BACTFRAGIL:        AGACACGGTCCAAACTCCT ACGGGAGGCAGCAGTGAGGAATATTGGTCAA 350
                                       PLK1
```

```
PSEUDAER:          A-TTGTAAAGCACTTTAAGTTGGGAGGAA[GGGCA---GTAAGTT-AATAC  463 SLK3
ACINBAUMANII:      G-TTGTAAAGCACTTTAAGCGAGGAGGAGG[CTAC---TTTAGTT-A[ATA[C  432 SLK4
LEGPNEU:           G-TTGTAAAGCACTTTCAGTGGGGAGGA[GGGTTG---ATAGGTT-AAGAG  443 SLK12
SERMAR:            G-TTGTAAAGCACTTTCAGCGAGGAGGAAGGTGG---TGAGCTT-AA[TAC  470 SLK11
ENTEROBACTAEROG:   G-TTGTAAAGT]ACTTTCAGCGAGGAGGA[AGGCGT--TAAGGTT-AATA[A  435 SLK18
KLEBSPNEU:         G-TTGTAAAGCACTTTCAGCGGGGAGGAAGG[CGA--TGAGGTT-AAT]AA  460 SLK10
ENTEROBACTCLOAC:   G-TTGTAAAGT]ACTTTCAGCGGGGAGGAGGA[AG[GCGA--CAGGGTT-AATAA  440 SLK9
ECOLI:             G-TTGTAAAGTACTTTCAGCGGGGAGGAA[G[GGAG--TAAAGTT-AATAC  468 SLK1
PROTVULG:          G-TTGTAAAGTACTTTCAGCGGGGAGGAA[GG[TTGA--TAAAGTT-AATAC  468 SLK13
HEMOINFLU:         G-TTGTAAAGTTCTTTCGGTATTGAGGA[AGGTTTG--ATGTGTT-AATAG  468 SLK8
MYCOBTUBERC:       G-TTGTAAACCTCTTTCACCATCGACGAAG[G[TC---CGGGTT---     461 SLK19
CORYNEYJEIJ:       -TTGTAA-CGCCTTTCGCTAG-GAAGAAG[CAC---TGTGT---         441 SLK17
ENTEROCOCFAECALI:  A-TCGTAAAACTCTGTTGTTAGAGAAGAACAAG[GAC-GTTAGTA-ACTG-  440 SLK7
ENTEROCOCFAECIUM:  A-TCGTAAAACTCTGTTGTTAGAGAAGAACAAG[GAT-GAGAGTA-ACTG-  440
STREPTPYOGEN:      A-TCGTAAAGCTCTGTTGTTAGAGAAGAATGA[TGGT-GGGAGTGGAAAA-  373 SLK15
STAPHEPI:          A-TCGTAAAACTCTGTTATTAGGGAAGA[ACAAATGT-GTAAGTA-ACTA-  450
STAPHAUREUS:       A-TCGTAAAACTCTGTTATTAGGGAA[GA[ACATATGT-GTAAGTA-ACTG-  462 SLK5
MYCOBACTPNEUM:     GATTGTAAAGTTCATTTATTTGGGAAGAAT[GACTTTAGCAGGT-AATGG  469 SLK16
BACTFRAGIL:        GGTCGTAAACTTCTTTTATATAAGAATAA[AG[TGCA--GTATGT--ATA-  444 SLK14
```

FIG. 12 (Part 1)

```
                                              |————————— ISN2* ——————————|
PSEUDAER:        CTTG]CTGTT]TTG-ACGTTAC       |CA-AC-AGAATAAGCACCGGCTAACTTCGT|   510
ACINBAUMANII:    CTAGAGATAG]TGGACGTTAC        |TC]-GC]AGAATAAGCACCGGCTAACTCTGT|  480
LEGPNEU:         CTGATTA-AC]TGGACGTTAC        |CC-AC-AGAAGAAGCACCGGCTAACTCCGT|   490
SERMAR:          GCTCATCAATTG-ACGTTAC         |TC]-G]C]-AGAAGAAGCACCGGCTAACTCCGT| 617
ENTEROBACTAEROG: CCTTGGCG]ATTG-ACGTTAC        |TC-GC]-AGAAGAAGCACCGGCTAACTCCGT|  482
KLEBSPNEU:       CCTCATCGATT]G-ACGTTAC        |CCTGC]-AGAAGAAGCACCGGCTAACTCCGT|  508
ENTEROBACTCLOAC: CCCTGT]CG]ATT]G-ACGTTAC      |CC-GC-AGAAGAAGCACCGGCTAACTCCGT|   487
ECOLI:           CTTTGCTC]A]T]TG-ACGTTAC      |CC-GC-AGAAGAAGCACCGGCTAACTCCGT|   516
PROTVULG:        CTTTGTCAA]TTG-AC]GTTAC       |CC-GC-AGAAGAAGCACCGGCTAACTCCGT|   615
HEMOINFLU:       CACATCAA]ATTG-AC]GTTAA       |AT-AC-AGAAGAAGCACCGGCTAACTCCGT|   516

MYCOBTUBERC:    -CT[CTCGGATTG-ACGGTA]GGTGG-AG]AAGAAGCACCGGCCAACTACGT     497
CORYNEYJEU:     ————GG-TG-ACGGTACCTG]GT-AC]AAGAAGCACCGGCTAACTACGT         481

ENTEROCOCFAECALI: -AACGTCCCCT]G]-ACGGTA       |TCTAACCAGAA--AGCCACGGCTAACTACGT|  488
ENTEROCOCFAECIUM: -TTCATCCCTTG]-ACGGTA        |TCTAACCAGAA--AGCCACGGCTAACTACGT|  486
STREPTPYOGEN:    -TCCACCAAGT]G-ACGGTA         |ACTAACCAGAA--AGGGACGGCTAACTACGT|  419
STAPHEPI:        -TGCACG]T]CTTG-ACGGTA        |CCTAATCAGAA--AGCCACGGCTAACTACGT|  496
STAPHAUREUS:     -TGCACA]T]CTTG-ACGGTA        |CCTAATCAGAA--AGCCACGGCTAACTACGT|  508
MYCOBACTPNEUM:   CT--AGAGTT]TG-ACTGTA         |CCA]-TTTTGAATAAGTGACGACTAACTATGT| 515
BACTFRAGIL:      ———CTGTTTTGT]AT]G-TA         |T]]A]AT—GAATAAGGATCGGCTAACTCCGT|  487
                                              |——————————— ISP2* ——————————|

PSEUDAER:        GCC |AGCAGCCGCGGTAATA| CGAAGGGTGCGAGCGTTAATCGGAATTACTG    560
ACINBAUMII:      GCC |AGCAGCCGCGGTAATA| CAGAGGGTGCGAGCGTTAATCGGATTTACTG    530
LEGPNEU:         GCC |AGCAGCCGCGGTAATA| CGGAGGGTGCGAGCGTTAATCGGAATTACTG    540
SERMAR:          GCC |AGCAGCCGCGGTAATA| CGGAGNGTGCAAGCGTTAATCGGAATTACTG    567
ENTEROBACTAEROG: GCC |AGCAGCCGCGGTAATA| CGGAGGGTGCAAGCGTTAATCGGAATTACTG    532
KLEBSPNEU:       GCC |AGCAGCCGCGGTAATA| CGGAGGGTGCAAGCGTTAATCGGAATTACTG    558
ENTEROBACTCLOAC: GCC |AGCAGCCGCGGTAATA| CGGAGGGTGCAAGCGTTAATCGGAATTACTG    537
ECOLI:           GCC |AGCAGCCGCGGTAATA| CGGAGGGTGCAAGCGTTAATCGGAATTACTG    585
PROTVULG:        GCC |AGCAGCCGCGGTAATA| CGGAGGGTGCAAGCGTTAATCGGAATTACTG    565
HEMOINFLU:       GCC |AGCAGCCGCGGTAATA| CGGAGNGTGCGAGCGTTAATCGGAATAACTG    566
MYCOMTUBERC:     GCC |AGCAGCCGCGGTAATA| CGTAGGGTGCGAGCGTTGTCCGGAATTACTG    647
CORYNEYJEU:      GCC |AGCAGCCGCGGTAATA| CGTAGGGTGCGA-CGTTGTCCGGAATTACTG    530
ENTEROCOCFAECALI:G]CC|AGCAGCCGCGGTAATA| CGTAGGTGGCAAGCGTTGTCCGGATTTATTG    536
ENTEROCOCFAECIUM:G]CC|AGCAGCCGCGGTAATA| CGTAGGTGGCAAGCGTTGTCCGGATTTATTG    536
STREPTPYOGEN:    G]CC|AGCAGCCGCGGTAATA| CGTAGGTCCCNAGCGTTGTCCGGATNTATTG    469
STAPHEPI:        G]CC|AGCAGCCGCGGTAATA| CGTAGGTGGCAAGCGTTATCCGGAATTATTG    546
STAPHAUREUS:     G]CC|AGCAGCCGCGGTAATA| CGTAGGTGGCAAGCGTTATCCGGAATTATTG    558
MYCOBACTPNEUM:   G]CC|AGCAGTCGCGGTAATA| CATAGGTCGACAAGCGTTATCCGGATTTATTG    555
BACTFRAGIL:      G]CC|AGCAGCCGCGGTAATA| CGGAGGATCCGAGCGTTATCCGGATTTATTG    637

ISP2* ———|       |———— PLK2H ————|
                 Region to which PLK2* binds

*Fluoresceine label
```

FIG. 12 (Part 2)

Abbreviations

| | | |
|---|---|---|
| l173758 | gb|M60300.1| | ASNRR5SS Aspergillus fumigatus |
| h70930 | gb|M60302.1| | YSASRSUA C.albicans |
| h76364 | gb|M60305.1| | YSASRSUD C.krusei |
| h76366 | gb|M60307.1| | YSASRSUF C.parapsilosis |
| h76367 | gb|M60308.1| | YSASRSUG C.tropicalis |
| h76457 | gb|M60311.1| | YBLSRSUA T.glabrata |

```
l176364 gb|M60305.1| YSASRSUD  GTCTTGTAATTGGAATGAGTACAATGTAAATACCTTAACGAGGATCA|ATT  536
l176457 gb|M60311.1| YSLSRSUA  GTCTTGTAATTGGAATGAGTACAATGTAAATACCTTAACGAGGAACA|ATT  547
l176366 gb|M60307.1| YSASRSUF  GTCTTGTAATTGGAATGAGTACAATGTAAATACCTTAACGAGGAACA|ATT  546
l176367 gb|M60308.1| YSASRSUG  GTCTTGTAATTGGAATGAGTACAATGTAAATACCTTAACGAGGAACA|ATT  545
l170930 gb|M60302.1| YSASRSUA  GTCTTGTAATTGGAATGAGTACAATGTAAATACCTTAACGAGGAACA|ATT  545
l173758 gb|M60300.1| ASNRR5SS  GTCTCGTAATTGGAATGAGTACAATCTAAATCCCTTAACGAGGAACA|ATT  545
                                                                              └─PFU1 l176364 gb|M60305.1| YSASRSUD  GGAGGGCAAGTCTGGT|CCAGCAGCCGCGGNAATTCCAGCTCCAATAGCG  586
l176457 gb|M60311.1| YSLSRSUA  GGAGGGCAAGTCTGGT|CCAGCAGCCGCGNNAATTCCAGCTCCAAAAGCG  597
l176366 gb|M60307.1| YSASRSUF  GGAGGGCAAGTCTGGT|CCAGCAGCCGCGGNAATTCCAGCTCCAAAAGCG  595
l176367 gb|M60308.1| YSASRSUG  GGAGGGCAAGTCTGGT|CCAGCAGCCGCGGNAATTCCAGCTCCAAAAGCG  595
l170930 gb|M60302.1| YSASRSUA  GGAGGGCAAGTCTGGT|CCAGCAGCCGCGGTAATTCCAGCTCCAAAAGCG  595
l173758 gb|M60300.1| ASNRR5SS  GGAGGGCAAGTCTGGT|CCAGCAGCCGCGGTAATTCCAGCTCCAATAGCG  595
                         PFU1─┘ l176364 gb|M60305.1| YSASRSUD  TATATTAAAGTTGTTGCAGTTAAAAAGCTCGTAGTTGAACTTTGGGCCTG  636
l176457 gb|M60311.1| YSLSRSUA  TATATTAAAGTTGTTGCAGTTAAAAAGCTCGTAGTTGAACTTTGGGCCTG  647
l176366 gb|M60307.1| YSASRSUF  TATATTAAAGTTGTTGCAGTTAAAAAGCTCGTAGTTGAACCTTGGGCTTG  645
l176367 gb|M60308.1| YSASRSUG  TATATTAAAGTTGTTGCAGTTAAAAAGCTCGTAGTTGAACCTTGGGCTTG  645
l170930 gb|M60302.1| YSASRSUA  TATATTAAAGTTGTTGCAGTTAAAAAGCTCGTAGTTGAACCTTGGGCTTG  645
l173758 gb|M60300.1| ASNRR5SS  TATATTAAAGTTGTTGCAGTTAAAAAGCTCGTAGTTGAACCTTGGGTCTG  645 l176364 gb|M60305.1| YSASRSUD  G - GCGGACGGTCTACCTATGG --- TAAGCACTGT - - TGCGGCCGGGTCTT  680
l176457 gb|M60311.1| YSLSRSUA  G - GTGGCCGGTCCGATTTTTT --- CGTGTACTGGAATGCAGCCGGGCCTT  693
l176366 gb|M60307.1| YSASRSUF  GCTTGGCCGGTCCATCTTTTTGATGCGTACTGGA - CCCAGCCGAGCCTT  694
l176367 gb|M60308.1| YSASRSUG  G - TTGGCCGGTCCATCTTTCT - GATGCGTACTGGA - CCCAACCGAGCCTT  692
l170930 gb|M60302.1| YSASRSUA  G - CTGGCCGGTCCATCTTTTT - GATGCGTACTGGA - CCCAGCCGAGCCTT  692
l173758 gb|M60300.1| ASNRR5SS  G - CTGGCCGGTCCGCCTCACC - - GCGAGTACTGG --- TCCGGCTGGACCT  690 l176364 gb|M60305.1| YSASRSUD  TCCTTCTGGGTASCCTCG-----------------GGCGAACCAGGAC     711
l176457 gb|M60311.1| YSLSRSUA  TCCTTCTGGCTAACCCCAAGTCCTTG--TGGCTTGGCGGCGAACCAGGAC  741
l176366 gb|M60307.1| YSASRSUF  TCCTTCTGGCTAGCCTTTT---------------GGCGAACCAGGAC     727
l176367 gb|M60308.1| YSASRSUG  TCCTTCTGGCTAGCCTTT----------------GGCGAACCAGGAC     724
l170930 gb|M60302.1| YSASRSUA  TCCTTCTGGGTAGCCATTTAT-------------GGCGAACCAGGAC     726
l173758 gb|M60300.1| ASNRR5SS  TCCTTCTGGGGAACCTCATGGCCTTCACTGGCTGTGGGGGAACCAGGAC   740
                                 SCA1, SCR1, SCT1, SCP2, STG1, SAU1 ← l176364 gb|M60305.1| YSASRSUD  TCTAGGACCATCGTAATGATTAATAGGGACGGTCG|GGGCATCAGTATTC  859
l176364 gb|M60305.1| YSASRSUD  TCTAGGACCATCGTAATGATTAATAGGGACGGTCG|GGGCATCAGTATTC  890
l176366 gb|M60307.1| YSASRSUF  TCTAGGACCATCGTAATGATTAATAGGGACGGTCG|GGGTATCAGTATTC  876
l176367 gb|M60308.1| YSASRSUG  TCTAGGACCATCGTAATGATTAATAGGGACGGTNG|GGGTATCAGTATTC  873
l170930 gb|M60302.1| YSASRSUA  TCTAGGACCATCGTAATGATTAATAGGGACGGTCG|GGGTATCAGTATTC  875
l173758 gb|M60300.1| ASNRR5SS  TCTAGGACCGCCGTAATGATTAATAGGGATAGTCG|GGGCGTCAGTATTC  869
                                        HP─────────────┘ └─────HP
                                                              HPS and HPA
```

FIG. 13 (Part 1)

```
h76384 gb M60305.1 YSASRSUD  AGTCGTCAGAGGTGAAAT TCTTGGATTGACTGAAGACTAACTACTGCGAA   908
h76384 gb M60305.1 YSASRSUD  AATTGTCAGAGGTGAAAT CTTGGATTTATTGAAGACTAACTACTGCGAA    940
h76366 gb M60307.1 YSASRSUF  AGTAGTCAGAGGTGAAAT TCTTGGATTTACTGAAGACTAACTACTGCGAA   926
h76367 gb M60308.1 YSASRSUG  AGTTGTCAGAGGTGAAAT TCTTGGATTTACTGAAGACTAACTACTGCGAA   923
h70930 gb M60302.1 YSASRSUA  AGTTGTCAGAGGTGAAAT TCTTGGATTTACTGAAGACTAACTACTGCGAA   925
h73756 gb M60300.1 ASNRRSSS  AGCTGTCAGAGGTGAAAT TCTTGGATTTGCTGAAGACTAACTACTGCGAA   938 h76384 gb M60305.1 YSASRSUD  CGAAGATGATCAGATACCGTCGTAGTCTTAACCATAAA CTATGCCGACTA  1008
h76384 gb M60305.1 YSASRSUD  CGAAGATGATCAGATACCGTCGTAGTCTTAACCATAAA CTATGCCGACTA  1039
h76366 gb M60307.1 YSASRSUF  CGAAGATGATCAGATACCGTCGTAGTCTTAACCATAAA CTATGCCGACTA  1025
h76367 gb M60308.1 YSASRSUG  CGAAGATGATCAGATACCGTCGTAGTCTTAACCATAAA CTATGCCGACTA  1022
h70930 gb M60302.1 YSASRSUA  CGAAGATGATCAGATACCGTCGTAGTCTTAACCATAAA CTATGCCGACTA  1024
h73756 gb M60300.1 ASNRRSSS  CGAAGACGATCAGATACCGTCGTAGTCTTAACCATAAA CTATGCCGACTA  1068 h76384 gb M60305.1 YSASRSUD  GGGATCGG GTGGTGCTACTNNG---CCCACTCGGCACCTNACGAGAAAT   1054
h76384 gb M60305.1 YSASRSUD  GGGATCGG GTGGTGYYYTTTTAGTGACCCACTCGGCACCTTACGAGAAAT   1069
h76366 gb M60307.1 YSASRSUF  GGGATCGG TTGTTGTTCTTTTATTGACGCAATCGGCACCTTACGAGAAAT   1075
h76367 gb M60308.1 YSASRSUG  GGGATCGG TTGTTGTTCTTTTATTGACGCAATCGGCACCTTACGAGAAAT   1072
h70930 gb M60302.1 YSASRSUA  GGGATCGG TTGTTGTTCTTTTATTGACGCAATCGGCACCTTACGAGAAAT   1074
h73756 gb M60300.1 ASNRRSSS  GGGATCGG GCGGTGTTTCTATGATGACCCGCTCGGCACCTTACGAGAAAT   1088
                             PFU2
```

FIG. 13 (Part 2)

SEQUENCE LISTING

<160> NUMBER OF SEQ ID NOS: 47

<210> SEQ ID NO 1
<211> LENGTH: 17
<212> TYPE: DNA
<213> ORGANISM: Artificial
<220> FEATURE:
<223> OTHER INFORMATION: consensus primer PLK2 old

<400> SEQUENCE: 1
tattaccgcg gctgctg                                                    17

<210> SEQ ID NO 2
<211> LENGTH: 18
<212> TYPE: DNA
<213> ORGANISM: Artificial
<220> FEATURE:
<223> OTHER INFORMATION: bacteria consensus primer (REV PLK2)
<220> FEATURE:
<221> NAME/KEY: misc_feature
<222> LOCATION: (17)..(17)
<223> OTHER INFORMATION: n is fluoresceine substituted t

<400> SEQUENCE: 2
gtattaccgc ggctgcng                                                   18

<210> SEQ ID NO 3
<211> LENGTH: 17
<212> TYPE: DNA
<213> ORGANISM: Artificial
<220> FEATURE:
<223> OTHER INFORMATION: bacteria consensus primer PLK1 old

<400> SEQUENCE: 3
ctacgggagg cagcagt                                                    17

<210> SEQ ID NO 4
<211> LENGTH: 19
<212> TYPE: DNA
<213> ORGANISM: Artificial
<220> FEATURE:
<223> OTHER INFORMATION: bacteria consensus primer FOR

<400> SEQUENCE: 4
tcctacggga ggcagcagt                                                  19

<210> SEQ ID NO 5
<211> LENGTH: 16
<212> TYPE: DNA
<213> ORGANISM: Artificial
<220> FEATURE:
<223> OTHER INFORMATION: bacteria consensus primer PLK1H

<400> SEQUENCE: 5
tacgggaggc agcagt                                           16

<210> SEQ ID NO 6
<211> LENGTH: 16
<212> TYPE: DNA
<213> ORGANISM: Artificial
<220> FEATURE:
<223> OTHER INFORMATION: bacteria consensus primer PLK2H
<220> FEATURE:
<221> NAME/KEY: misc_feature
<222> LOCATION: (16)..(16)
<223> OTHER INFORMATION: n is fluoresceine substituted t

<400> SEQUENCE: 6
tattaccgcg gctgcn                                           16

<210> SEQ ID NO 7
<211> LENGTH: 20
<212> TYPE: DNA
<213> ORGANISM: Artificial
<220> FEATURE:
<223> OTHER INFORMATION: fungal consensus forward primer PFU1

<400> SEQUENCE: 7
attggagggc aagtctggtg                                       20

<210> SEQ ID NO 8
<211> LENGTH: 20
<212> TYPE: DNA
<213> ORGANISM: Artificial
<220> FEATURE:
<223> OTHER INFORMATION: fungal consensus backward primer PFU 2

<400> SEQUENCE: 8
ccgatcccta gtcggcatag                                       20

<210> SEQ ID NO 9
<211> LENGTH: 20
<212> TYPE: DNA
<213> ORGANISM: Artificial
<220> FEATURE:
<223> OTHER INFORMATION: consensus forward upper primer AR3

<400> SEQUENCE: 9
gcggtgaaat gcgtagagat                                       20

<210> SEQ ID NO 10
<211> LENGTH: 20
<212> TYPE: DNA
<213> ORGANISM: Artificial
<220> FEATURE:
<223> OTHER INFORMATION: consensus backward lower primer AR4

<400> SEQUENCE: 10
gtttacggcg tggactacca                                       20

<210> SEQ ID NO 11

```
<211> LENGTH: 26
<212> TYPE: DNA
<213> ORGANISM: Artificial
<220> FEATURE:
<223> OTHER INFORMATION: probe - specific for E.coli SLK1

<400> SEQUENCE: 11
agggagtaaa gttaataacct ttgctc                                        26

<210> SEQ ID NO 12
<211> LENGTH: 27
<212> TYPE: DNA
<213> ORGANISM: Artificial
<220> FEATURE:
<223> OTHER INFORMATION: probe - specific for Staphylococcus epi.  SLK
      2

<400> SEQUENCE: 12
gaacaaatgt gtaagtaact atgcacg                                        27

<210> SEQ ID NO 13
<211> LENGTH: 25
<212> TYPE: DNA
<213> ORGANISM: Artificial
<220> FEATURE:
<223> OTHER INFORMATION: probe - specific for Pseudomonas SLK 3

<400> SEQUENCE: 13
ggaagggcag taagttaata ccttg                                          25

<210> SEQ ID NO 14
<211> LENGTH: 26
<212> TYPE: DNA
<213> ORGANISM: Artificial
<220> FEATURE:
<223> OTHER INFORMATION: probe - specific for Acinobacter baumanii SLK 4

<400> SEQUENCE: 14
atacctagag atagtggacg ttactc                                         26

<210> SEQ ID NO 15
<211> LENGTH: 27
<212> TYPE: DNA
<213> ORGANISM: Artificial
<220> FEATURE:
<223> OTHER INFORMATION: probe - specific for Staph. aureus SLK 5

<400> SEQUENCE: 15
gaacatatgt gtaagtaact gtgcaca                                        27

<210> SEQ ID NO 16
<211> LENGTH: 25
<212> TYPE: DNA
<213> ORGANISM: Artificial
<220> FEATURE:
<223> OTHER INFORMATION: probe - specific for Enterococcus faecium SLK 6

<400> SEQUENCE: 16
gatgagagta actgttcatc ccttg                                          25

<210> SEQ ID NO 17
<211> LENGTH: 24
<212> TYPE: DNA
<213> ORGANISM: Artificial
<220> FEATURE:
<223> OTHER INFORMATION: probe specific for Enterococcus faecalis SLK 7
```

```
<400> SEQUENCE: 17
gacgttagta actgaacgtc ccct                                          24

<210> SEQ ID NO 18
<211> LENGTH: 28
<212> TYPE: DNA
<213> ORGANISM: Artificial
<220> FEATURE:
<223> OTHER INFORMATION: probe specific for Haemophilus influ. SLK 8

<400> SEQUENCE: 18
tgatgtgtta atagcacatc aaattgac                                      28

<210> SEQ ID NO 19
<211> LENGTH: 25
<212> TYPE: DNA
<213> ORGANISM: Artificial
<220> FEATURE:
<223> OTHER INFORMATION: probe - specific for  Enterobacter cloacae SKL
      9

<400> SEQUENCE: 19
gacagggtta ataaccctgt cgatt                                         25

<210> SEQ ID NO 20
<211> LENGTH: 26
<212> TYPE: DNA
<213> ORGANISM: Artificial
<220> FEATURE:
<223> OTHER INFORMATION: probe - specific for Klebsiella pneumoniae SLK
      10

<400> SEQUENCE: 20
cgatgaggtt aataacctca tcgatt                                        26

<210> SEQ ID NO 21
<211> LENGTH: 26
<212> TYPE: DNA
<213> ORGANISM: Artificial
<220> FEATURE:
<223> OTHER INFORMATION: probe specific for Serratia SLK 11

<400> SEQUENCE: 21
aatacgctca tcaattgacg ttactc                                        26

<210> SEQ ID NO 22
<211> LENGTH: 26
<212> TYPE: DNA
<213> ORGANISM: Artificial
<220> FEATURE:
<223> OTHER INFORMATION: probe  specific for Legionella pneu SLK 12

<400> SEQUENCE: 22
ggttgatagg ttaagagctg attaac                                        26

<210> SEQ ID NO 23
<211> LENGTH: 29
<212> TYPE: DNA
<213> ORGANISM: Artificial
<220> FEATURE:
<223> OTHER INFORMATION: probe - specific for Proteus vulgaris SLK 13

<400> SEQUENCE: 23
tgataaagtt aatacctttg tcaattgac                                     29
```

<210> SEQ ID NO 24
<211> LENGTH: 29
<212> TYPE: DNA
<213> ORGANISM: Artificial
<220> FEATURE:
<223> OTHER INFORMATION: probe - specific for Bacteroides fragilis SLK
      14

<400> SEQUENCE: 24
tgcagtatgt atactgtttt gtatgtatt                                    29

<210> SEQ ID NO 25
<211> LENGTH: 24
<212> TYPE: DNA
<213> ORGANISM: Artificial
<220> FEATURE:
<223> OTHER INFORMATION: probe - specific for Streptococcus pyogenes SLK
      15

<400> SEQUENCE: 25
gtgggagtgg aaaatccacc aagt                                         24

<210> SEQ ID NO 26
<211> LENGTH: 26
<212> TYPE: DNA
<213> ORGANISM: Artificial
<220> FEATURE:
<223> OTHER INFORMATION: probe - specific for Mycobact. pneum. SLK 16

<400> SEQUENCE: 26
gtaatggcta gagtttgact gtacca                                       26

<210> SEQ ID NO 27
<211> LENGTH: 22
<212> TYPE: DNA
<213> ORGANISM: Artificial
<220> FEATURE:
<223> OTHER INFORMATION: probe - specific for Corynebact. Jejuni SLK 17

<400> SEQUENCE: 27
cactgtgtgg tgacggtacc tg                                           22

<210> SEQ ID NO 28
<211> LENGTH: 24
<212> TYPE: DNA
<213> ORGANISM: Artificial
<220> FEATURE:
<223> OTHER INFORMATION: probe - specific for Enterobacter aerog SLK 18

<400> SEQUENCE: 28
accttggcga ttgacgttac tcgc                                         24

<210> SEQ ID NO 29
<211> LENGTH: 24
<212> TYPE: DNA
<213> ORGANISM: Artificial
<220> FEATURE:
<223> OTHER INFORMATION: probe - specific for Mycobact. tuberculosis SLK
      19

<400> SEQUENCE: 29
ctctcggatt gacggtaggt ggag                                         24

<210> SEQ ID NO 30
<211> LENGTH: 22
<212> TYPE: DNA
<213> ORGANISM: Artificial

```
<220> FEATURE:
<223> OTHER INFORMATION: gram-negative probe SKN1

<400> SEQUENCE: 30
gaggcagcag tgggaatat tg                                              22

<210> SEQ ID NO 31
<211> LENGTH: 22
<212> TYPE: DNA
<213> ORGANISM: Artificial
<220> FEATURE:
<223> OTHER INFORMATION: gram-positive probe SKP1

<400> SEQUENCE: 31
gaggcagcag tagggaatct tc                                             22

<210> SEQ ID NO 32
<211> LENGTH: 30
<212> TYPE: DNA
<213> ORGANISM: Artificial
<220> FEATURE:
<223> OTHER INFORMATION: gram-positive probe ISP 2*
<220> FEATURE:
<221> NAME/KEY: misc_feature
<222> LOCATION: (30)..(30)
<223> OTHER INFORMATION: n is g modified with fluorescent dye LC 705

<400> SEQUENCE: 32
cctaaccaga aagccacggc taactacgtn                                     30

<210> SEQ ID NO 33
<211> LENGTH: 24
<212> TYPE: DNA
<213> ORGANISM: Artificial
<220> FEATURE:
<223> OTHER INFORMATION: gram-negative probe ISP
<220> FEATURE:
<221> NAME/KEY: misc_feature
<222> LOCATION: (22)..(22)
<223> OTHER INFORMATION: n is t modified with fluorescent dye LC 705

<400> SEQUENCE: 33
agaaagccac ggctaactac gngc                                           24

<210> SEQ ID NO 34
<211> LENGTH: 23
<212> TYPE: DNA
<213> ORGANISM: Artificial
<220> FEATURE:
<223> OTHER INFORMATION: gram-negative probe ISN
<220> FEATURE:
<221> NAME/KEY: misc_feature
<222> LOCATION: (21)..(21)
<223> OTHER INFORMATION: n is t modified with fluorescent dye LC 640

<400> SEQUENCE: 34
agaagcaccg gctaactccg ngc                                            23

<210> SEQ ID NO 35
<211> LENGTH: 30
<212> TYPE: DNA
<213> ORGANISM: Artificial
<220> FEATURE:
<223> OTHER INFORMATION: probe for Candida albicans Scal

<400> SEQUENCE: 35
tctgggtagc catttatggc gaaccaggac                                     30
```

<210> SEQ ID NO 36
<211> LENGTH: 30
<212> TYPE: DNA
<213> ORGANISM: Artificial
<220> FEATURE:
<223> OTHER INFORMATION: probe for Candida krusei SCKI

<400> SEQUENCE: 36
gtctttcctt ctggctagcc tcgggcgaac                                30

<210> SEQ ID NO 37
<211> LENGTH: 30
<212> TYPE: DNA
<213> ORGANISM: Artificial
<220> FEATURE:
<223> OTHER INFORMATION: probe for Candida parapsilosis SCPI

<400> SEQUENCE: 37
tttccttctg gctagccttt ttggcgaacc                                30

<210> SEQ ID NO 38
<211> LENGTH: 30
<212> TYPE: DNA
<213> ORGANISM: Artificial
<220> FEATURE:
<223> OTHER INFORMATION: probe for Candida tropiealis Sctl

<400> SEQUENCE: 38
gttggccggt ccatctttct gatgcgtact                                30

<210> SEQ ID NO 39
<211> LENGTH: 30
<212> TYPE: DNA
<213> ORGANISM: Artificial
<220> FEATURE:
<223> OTHER INFORMATION: probe for Torulopsis glabrata Stg 1

<400> SEQUENCE: 39
ttctggctaa ccccaagtcc ttgtggcttg                                30

<210> SEQ ID NO 40
<211> LENGTH: 30
<212> TYPE: DNA
<213> ORGANISM: Artificial
<220> FEATURE:
<223> OTHER INFORMATION: probe for Aspergillus SAUI

<400> SEQUENCE: 40
catggccttc actggctgtg gggggaacca                                30

<210> SEQ ID NO 41
<211> LENGTH: 25
<212> TYPE: DNA
<213> ORGANISM: Artificial
<220> FEATURE:
<223> OTHER INFORMATION: general fungal probe 1 HPA

<400> SEQUENCE: 41
ctgaatgatt aatagggacg gtcgg                                     25

<210> SEQ ID NO 42
<211> LENGTH: 30
<212> TYPE: DNA
<213> ORGANISM: Artificial
<220> FEATURE:
<223> OTHER INFORMATION: general fungal probe 2 HPS

```
<220> FEATURE:
<221> NAME/KEY: misc_feature
<222> LOCATION: (1)..(1)
<223> OTHER INFORMATION: n is g modified with fluoresceine

<400> SEQUENCE: 42
ngtatcagta ttcagttgtc agaggtgaaa                                              30

<210> SEQ ID NO 43
<211> LENGTH: 31
<212> TYPE: DNA
<213> ORGANISM: Artificial
<220> FEATURE:
<223> OTHER INFORMATION: ISN2 internal probe negative
<220> FEATURE:
<221> NAME/KEY: misc_feature
<222> LOCATION: (31)..(31)
<223> OTHER INFORMATION: n is c, labeled with LC 640

<400> SEQUENCE: 43
accgcagaat aagcaccggc taactccgtg n                                            31

<210> SEQ ID NO 44
<211> LENGTH: 28
<212> TYPE: DNA
<213> ORGANISM: Artificial
<220> FEATURE:
<223> OTHER INFORMATION: probe for gram-negative bacteria ISN2*
<220> FEATURE:
<221> NAME/KEY: misc_feature
<222> LOCATION: (28)..(28)
<223> OTHER INFORMATION: n is t, substituted with LC 640

<400> SEQUENCE: 44
ccgcagaata agcaccggct aactccgn                                                28

<210> SEQ ID NO 45
<211> LENGTH: 30
<212> TYPE: DNA
<213> ORGANISM: Artificial
<220> FEATURE:
<223> OTHER INFORMATION: probe for gram-positive bacteria ISP2*
<220> FEATURE:
<221> NAME/KEY: misc_feature
<222> LOCATION: (30)..(30)
<223> OTHER INFORMATION: n is g, substituted by LC 705

<400> SEQUENCE: 45
cctaaccaga aagccacggc taactacgtn                                              30

<210> SEQ ID NO 46
<211> LENGTH: 31
<212> TYPE: DNA
<213> ORGANISM: Artificial
<220> FEATURE:
<223> OTHER INFORMATION: probe for gram-positive bacteria ISP2
<220> FEATURE:
<221> NAME/KEY: misc_feature
<222> LOCATION: (31)..(31)
<223> OTHER INFORMATION: n is c, substituted by LC 705

<400> SEQUENCE: 46
cctaatcaga aagcgacggc taactacgtg n                                            31

<210> SEQ ID NO 47
<211> LENGTH: 17
<212> TYPE: DNA
<213> ORGANISM: Artificial
<220> FEATURE:
```

-continued

```
<223> OTHER INFORMATION: primer IFL
<220> FEATURE:
<221> NAME/KEY: misc_feature
<222> LOCATION: (16)..(16)
<223> OTHER INFORMATION: n is t, substituted by fluoresceine

<400> SEQUENCE: 47
tattaccgcg gctgcng                                                    17
```

OLIGONUCLEOTIDES FOR RAPIDLY IDENTIFYING MICROBIAL DNA OR RNA

CROSS-REFERENCE TO RELATED APPLICATIONS

This application is a Continuation application of application Ser. No. 10/168,639 filed Jul. 24, 2002, now U.S. Pat. No. 7,169,555 which is the United States national phase application under 35 USC 371 of International application PCT/DE00/04610 filed Dec. 27, 2000.

BACKGROUND OF THE INVENTION

1. Field of the Invention

The invention relates to a method for rapidly identifying microbial DNA/RNA; to a kit for this purpose and the use of the method.

2. Background Information

The rapid identification of microorganisms, in particular the frequently occurring bacteria, viruses and fungi, is of general interest, for example, in connection with foodstuffs and also water, criminalistics, etc. However, a particularly important area of use is that of clinical diagnosis, particularly in the case of intensive care patients who are suffering from severe bacterial infections and who are at high risk of incurring severe organ damage within the context of a systemic inflammatory reaction and of even dying from it. The mortality rate in connection with severe sepsis, septic shock and multi-organ failure is up to 90%. No early parameters, which can be determined in the chemical laboratory and which indicate the beginning of an infection, even of a severe systemic infection, are currently available. Currently available routine parameters of inflammation, such as increase in leukocyte count or increase in C-reactive protein, only respond to a systemic infection with a chronological delay of from 1 to 3 days, are not specific to this infection and may be increased even in the absence of an infection with microorganisms. However, it would be extremely desirable to be also able to rapidly identify microorganisms in connection with local infections, for example, eye infections, also after eye operations, which can otherwise even lead to the loss of the eye which has been operated on, parodontitis and also local fungal infections. Early diagnosis of an infection is essential for providing the possibility of early therapy. In particular, it is important to identify the infecting microorganism at an early stage in order to be able to initiate selective antibiotic therapy. However, the conventional microbiological diagnosis by means of propagation and culture detection is not satisfactory in this context. In the first place, this detection frequently takes several days and, in the second place, this type of detection is only possible when live bacteria are present in the sample which is provided. However, since body fluids, in particular blood, possess bactericidal properties, this is frequently not the case even when there is an infection. Conventional microbiological diagnosis therefore suffers from a high rate of falsely negative findings. Rapid diagnosis of an infection, and rapid identification of the infecting microorganism, would therefore mean the possibility of early therapy which was specifically oriented toward the organism which had been found and therefore gave grounds for the hope of being able to exert a favorable influence on the severity of the disease and even on the mortality rate of the disease.

STATE OF THE ART

It is known that bacterial and fungal DNA/ can be amplified nonspecifically by PCR using consensus primers such that, even when only the smallest traces of the DNA/RNA are present, sufficient quantities for detection are prepared from these small quantities (ROCHE LightCycler directions). The double-stranded DNA which has thus been prepared in sufficient quantity for customary detection methods can then be qualitatively, selectively and quantitatively detected as such.

The presence of microbial DNA/RNA can be qualitatively detected, for example, using intercalating agents which only bind to double-stranded DNA and, on binding, emit a signal which indicates binding. Specific detection can also be effected using specific probes which only bind to DNA/RNA of particular species; if a microorganism other than the presumed one is present in the sample, it is then necessary to carry out experiments using different specific probes until one probe fits, that is indicates specific binding. Consequently, current methods only provide information, in the first PCR run, that RNA/DNA of bacterial or fungal origin is present; the specification itself is a further, elaborate process of searching which is only defined by empirical values.

WO 97/07238 describes the amplification of fungal DNA from clinical material (blood) using consensus primers, which, by means of PCR, amplify a region of the 18 ssu rRNA, and subsequent specific identification of the amplified fungal DNA by means of Southern blotting. In order to explain PCR and avoid repetitions, the entire disclosure of this document is hereby incorporated by reference.

In the case of bacteria, consensus primers which bind to highly conserved regions of bacterial DNA, for example the highly conserved 16 S region of the rRNA or else the likewise highly conserved 23 S region of the rDNA, are also known. The corresponding templates can be amplified using suitable consensus primers and the bacterial DNA which has been amplified in this way can then be detected by means of various detection methods (Anthony, Brown, French; J. Clin. Microbiol. 2000, pp. 781-788 "Rapid Diagnosis of Bacteremia by universal amplification of 23S Ribosomal DNA followed by Hybridization to an Oligonucleotide Array and WO 00/66777).

WO 00/66777 proposes, as do Woo, Patel et al. in Anal. Biochem. 1998, 259 and in J. Microbiol. Methods 1999, 23-30, using bacteria-specific primers; in this way only amplifying specific bacteria and then determining the melting point of the only double-stranded DNA which has been amplified by the special primers, and which has been labeled with intercalating substances, in this instance usually SYBR GREEN, in order to once again identify the DNA which has been amplified using the specific primers, since the melting points of probe/DNA hybridization products are typical. This is also known for herpes viruses (HSV)—Espyl, Uhl et al. J. Clin. Microbiol. 2000, pp. 795 ff.; this document uses suitable primers for specifically amplifying the thymidine kinase gene of the virus and subsequently uses melting curve analysis to once again verify the amplified DNA which has been identified using the primers. The specific primers which are used in this publication do not bind exclusively to consensus regions but, rather, to quite specific sequences such that only the latter are amplified. It is not possible to use this method to detect the presence of further microorganisms alongside each other.

In J. Clin. Microbiol. 1999, pp. 464-466 "Gram-Type Specific Broad-Range PCR Amplification for Rapid Detection of 62 Pathogenic Bacteria", Klausegger et al. show that the DNA/RNA of Gram-positive bacteria can be amplified in a group-specific manner in a PCR using specially designed Gram-positive primers and that the Gram-negative bacteria are not amplified in this PCR, such that it is at least possible to subdivide the bacteria under investigation into Gram-positive bacteria and Gram-negative bacteria.

Klausegger uses conventional microbiological methods for further specifying the Gram-positive bacteria which have been amplified in this way. According to Klausegger, it is at least possible to treat pathogenic bacteria rapidly, with this treatment being directed towards Gram-positive bacteria or Gram-negative bacteria. However, the Klausegger publication does not permit any more precise identification within a short period of time.

The amplification of bacterial rRNA is in no way restricted to the 16S region or the 23S region; it is also known that, in bacteria, it is possible to amplify the "spacer region" between the 16 S and 23S genes in the prokaryotic rRNA using special primers which are suitable for this purpose (App . . . and Environmental Microbiology, 1993, pp. 945-952); the "spacer region" lies between two highly conserved regions on each of which a primer then lies.

The methods of the prior art consequently only made it possible, in a single PCR, to detect microorganisms using consensus primers, without the microorganisms being classified in any way, or else to detect a single microorganism. An elaborate method was still required for determining the microorganism species since a very wide variety of possible probes had to be tested out or else the determination had to be effected using the customary microbiological detection procedure.

The object of the invention is now to enable microbial DNA/RNA to be quantified and qualified more rapidly than has previously been the case.

SUMMARY OF THE INVENTION

According to the present invention, the above object is achieved by means of a method having the features set forth hereinbelow.

The following is consequently employed for determining microbial DNA/RNA:

providing a sample containing RNA/DNA nonspecifically amplifying the microbial DNA/RNA by means of a PCR (polymerase chain reaction) method using generic consensus primers analyzing the physical properties of the amplified consensus sequence (e.g. by carrying out a melting point analysis in the SYBR Green format or else by binding multifunctional probes)

where appropriate, adding a labeled oligonucleotide/ probe carrying out further specification by analyzing the physical properties of the DNA/RNA oligonucleotide complex, such as the temperature dependence of the hybridization, or else by introducing special probes and using Fltc to analyze the behavior of the probes when binding to the DNA, for example by carrying out a melting point analysis of the temperature dependence of the probe binding behavior, for the purpose of further specifying the microorganism to be identified.

It is advantageous if the PCR method is a real-time PCR method since this makes it possible, in the same PCR run, to specify the identified microorganism at the same time as quantifying the RNA/DNA which is present in the sample.

In particular, the use of the very sensitive and quantitative real-time PCR to detect microbial genomic DNA enables a microbial infection to be detected in the chemical laboratory at a very early stage.

Examples of suitable samples for investigation are body fluids, smears or homogenized tissue and also all other materials in which DNA residues are to be detected. Since, as a rule, the infecting microorganism is a priori unknown, it is appropriate, in the PCR, to use primers which can be employed for amplifying, as nonspecifically as possible, the DNA/RNA which is present in, if at all possible, all the microorganisms which are to be taken into consideration for the diagnosis.

Another aspect of the invention relates to a kit for rapidly identifying microbial DNA/RNA in samples, comprising decontaminated polymerase; solution containing a standard DNA/RNA concentration of a known DNA/RNA template. In a preferred embodiment, the kit additionally contains at least one DNA/RNA oligonucleotide probe. For use in the method according to the invention, these special DNA/RNA probes can also be sold individually for identifying specific microorganisms.

In addition, the invention also relates to a method or a program which enables automated machines which are suitable for carrying out a real-time PCR to also be used for detecting and identifying microorganisms.

The distinctive feature of the method according to the invention is that, with the microorganism being unknown, a nonspecific amplification using consensus primers is first of all carried out, with the DNA segments which are amplified between the consensus primers exhibiting differences which are specific for the respective bacteria. These differences, which are typical for each bacterium, can be used (after nonspecific amplification) for identifying and specifying the microorganism which is actually present.

After the DNA/RNA in the sample has been amplified nonspecifically, the infecting microorganism can be identified and specified using a variety of methods, some examples of which are listed as follows:

A. Reverse dot blot

B. DNA/RNA microchip or microarray technique

C. Analysis of the melting curve of the total amplified DNA/RNA sequence

D. Hybridization of the amplificate with labeled oligonucleotide probes, advantageously during a PCR E. Melting curve analysis of the hybridized oligonucleotide probes F. Combination of the methods listed under C-E.

With regard to A

The DNA/RNA microchip technique is disclosed, for example, in Cnvynne P. and Page G. Microarray analysis, the next revolution in Molecular Biology Science 1999, or in Sinclair B. "Everything's Great When it sits on a Chip—a Bright future for DNA arrays", The Scientist 1999, May 24,13(11) 18-20.

With regard to B

Reverse dot blot is known.

With regard to C

The simplest and most rapid method for carrying out a rough preclassification of the infecting microorganism is that of analyzing the melting temperature of the entire amplificate. This makes it possible to carry out a simple differentiation into groups such as Gram-positive or Gram-negative bacteria.

With regard to D

It is furthermore possible to carry out a specification, using special fluorescent dye-labeled oligonucleotides, in connection with performing a real-time PCR. It is furthermore possible to use the combined information from the melting curve analysis of the amplified DNA segments and the behavior when binding to specific oligonucleotide probes for specifying more precisely.

With regard to E

On top of this, the information which is obtained from the melting temperature analysis of the oligonucleotide probes can also be used for specifying.

With regard to F

Finally, it is possible to use the information which is obtained from all the abovementioned analytical methods in combination for very precisely identifying the infecting microorganism.

It is consequently possible, by selecting special probes and analyzing melting curves of the hybridization products on the microbial DNA, to determine very rapidly which DNA is present. In this connection, it is not necessary to prepare a specific probe for each bacterium; instead, conclusions with regard to the nature of the microorganism can be drawn with the aid of a few probes and the melting points of the hybridization product. Surprisingly, it is possible, in this way, in only one analytical run on the online PCR, not only to quantitatively detect the microbial DNA but also, following the amplification, to identify a large number of different microorganisms by performing analyses with a few oligonucleotides.

According to one of the claims, a preferred use of the method is that of rapidly identifying microbial genomic DNA in intensive-care patients, in particular. In contrast to the conventional microbiological detection using culture techniques, which as a rule take several days, the method which is presented here can be carried out using online PCR in less than 3 hours. This speeds up diagnosis enormously and consequently provides the possibility of carrying out selective therapy at a substantially earlier time point.

However, the method can be employed anywhere where microbial contamination has to be quantified and qualified rapidly, for example in criminalistics and also in foodstuff testing, etc.

The invention is explained below more specifically with the aid of the accompanying drawing and of examples, to which it is, however, in no way restricted but which are intended to improve understanding of the invention.

BRIEF DESCRIPTION OF THE DRAWINGS

FIG. 1: shows melting curves of SYBR Green-labeled total PCR products from 4 bacteria, with the fluorescence intensity being plotted as a function of the temperature and the first derivative of this curve, dI/dT, also being plotted;

FIG. 1a: depicts the melting points of various bacterial species using SYBR Green FIG. 1b: depicts the melting points of patient samples using SYBR Green FIG. 1c: depicts the course of the PCR of the patient samples in the SYBR Green format FIG. 2: depicts the amplification of bacterial DNA by the growing fluorescence signal of a Gram-neg. and Gram-pos.-binding probe at the end of the annealing phase of the PCR cycle;

FIG. 3: shows melting curves of the hybridization product obtained from amplified DNA and a specific fluorescence-labeled hybridization probe for Gram-positive organisms (fluorescence intensity in dependence on the temperature, or the first derivative of the curve (below)).

FIG. 4: shows melting curves as in FIG. 3 but using a probe for Gram-negative organisms FIG. 5: shows melting curves of the hybridization product obtained from the amplified genomic DNA of various Gram-negative organisms and a Gram-negative probe FIG. 6 shows melting curves of the hybridization product obtained from genomic DNA amplified with labeled primers and Gram(+) probes FIG. 7 shows melting curves of hybridization products obtained from Gram-positive hybridization probes and mixtures of *Pseudomonas* and *Staph. epi*

FIG. 12: shows an alignment of bacterial 16rRNA with the position of primers and probes FIG. 13: shows the alignment of fungal RNA with the position of primers and probes

DETAILED DESCRIPTION OF THE INVENTION

A determining the microorganism nucleotide

Figure 8:
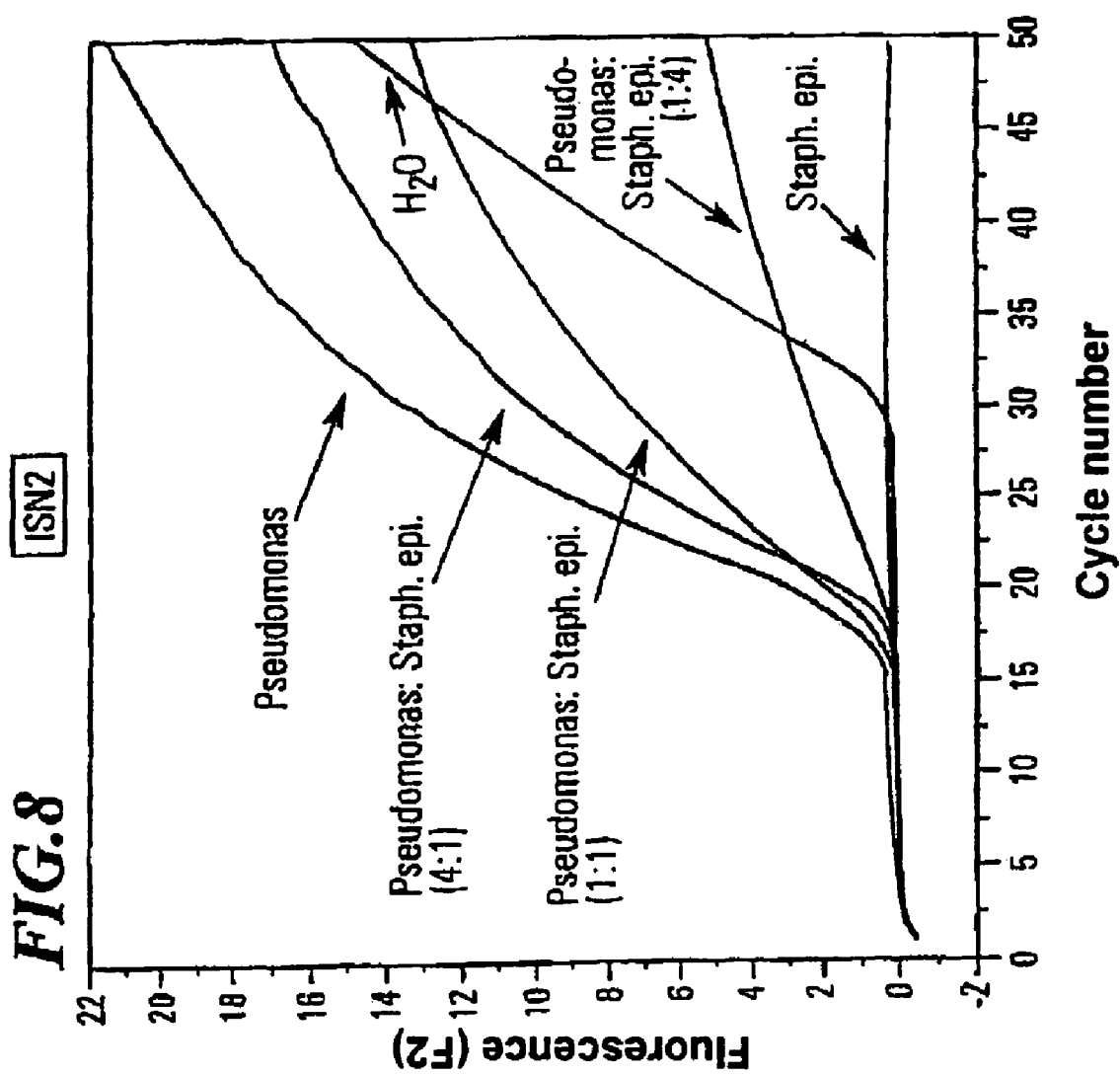
FIG. 8 shows melting curves of hybridization products obtained from Gram-neg. hybridization probes and mixtures of *Pseudomonas* and *Staph. epi*

Analyzing the melting points of double-stranded nucleotides from bacteria

Many of the following experiments were carried out using pure cultures of bacterial strains from the following list, which strains are, in the inventors' experience, frequently to be found in hospitals; the "RK" abbreviations employed appear in the drawings, which are print-outs from the Light-Cycler program:

| Abbreviation | Microorganism | ATCC number |
|---|---|---|
| RK1 | *Pseudomonas aeruginosa* | 27852 |
| RK2 | *Klebsiella pneumoniae* | 9591 |
| RK3 | *Serratia marcescens* | 264 |
| RK4 | *Escherichia coli* | 25922 |
| RK5 | *Proteus vulgaris* | 6361 |
| RK6 | *Haemophilus influenzae* | 8142 |
| RK7 = | *Enterococcus faecalis* | 11420 |
| RK8 = | *Enterococcus faecium* | 19579 |
| RK9 = | *Enterobacter aerogenes* | 29007 |
| RK10 = | *Enterobacter cloacae* | 27508 |
| RK11 = | *Streptococcus pyogenes* | 8668 |
| RK12 = | *Staphylococcus epidermidis* | 14990 |
| RK13 = | *Staphylococcus aureus* | 6538 |
| RK14 = | *Bacteroides fragilis* | 25285 |
| RK15 = | *Mycobacterium tuberculosis* | 25177 |
| RK16 = | *Acinetobacter baumannii* | 9955 |
| RK17 = | *Legionella pneumophila* | 33152 |
| RK18 = | *Candida albicans* | 10231 |
| RK19 = | *Aspergillus fumigatus* | 1022 |

FIG. 1 shows the melting curve analysis of the SYBR Green-labeled PCR product from four different bacteria, with the fluorescence intensity of the SYBR Green being plotted as a function of the temperature, or the first derivative of the intensity in accordance with the temperature being plotted (in the lower part of the figure). In each case, DNA from a pure-culture strain of the following bacteria [lacuna] was amplified over YY cycles, as described in ex. [lacuna] and, at the end of the amplification, a melting curve was determined using SYBR Green. The middle of the peak was taken to be the melting point. FIG. 1 clearly shows that, even when using a consensus primer, in this specific case for the 16 S RNA region, the resulting PCR products, i.e. double-stranded DNA, exhibit physical properties which are different for different bacterial groups, in particular different melting temperatures. This is also evident from FIG. 1a, which lists the melting points of double-stranded DNA from fifteen of the bacteria which occur most commonly in hospitals. Whereas the melting temperature is in the region of 86.35 degrees C. in the case of *Pseudomonas aeruginosa*, the melting temperatures of *Proteus vulgaris* (approx. 86.9 degrees C.), *Serratia marcescens* (approx. 87.75 degrees C.) and *Klebsiella pneumonia* (approx. 88.4 degrees C.) can be clearly distinguished from this. It is consequently already possible, by analyzing the melting temperature curves of the PCR amplificate, to subdivide the groups of bacteria which may possibly be present into at least 4 groups. The reproducibility of the melting curves is excellent, as is evident from the following table:

Reproducibility of the melting points:

| Bacterium | Experiment No. | M.p. of the dsDNA |
|---|---|---|
| *Pseudomonas aer.* | 1 | 83.36 |
| *Pseudomonas aer.* | 2 | 86.36 |
| *Pseudomonas aer.* | 3 | 86.34 |
| *Klebsiella pneum.* | 1 | 88.49 |
| *Klebsiella pneum.* | 2 | 88.42 |
| *Klebsiella pneum.* | 3 | 88.36 |
| *Serratia marc.* | 1 | 87.78 |
| *Serratia marc.* | 2 | 87.70 |
| *Serratia marc.* | 3 | 87.71 |
| *Proteus vulg.* | 1 | 86.92 |
| *Proteus vulg.* | 2 | 86.90 |
| *Proteus vulg.* | 3 | 86.93 |

Designing probes/primer combinations

Since, according to the invention, microorganism DNA/RNA is amplified nonspecifically, the choice or the design of suitable primers and probes is important for more precisely classifying the microorganisms and thereby implementing the invention. Programs such as the Shareware "GENE-FISHER" program are helpful in providing suggestions for the selection and/or design of primers and probes. This program looks for DNA/RNA consensus regions and then proposes appropriate primers in accordance with specification or else probes, in accordance with the region specified, and their properties.

Primers

It is known that certain gene sequence fragments within most bacteria or most fungi are essentially identical; these sequence fragments are termed conserved regions. Because of these conserved regions, it is possible to use "consensus primers", which bind to these regions, to amplify the RNA/DNA of these microorganisms non-specifically, with, in a preferred embodiment of the invention, a region which is specific for the microorganism, and to which specialized probes can then bind, having, in this present case, to be located between the conserved regions. Such regions are known, and the skilled person can then seek out suitable regions for primers. It is important that the primers are not too long, inter alia because the desired nonspecificity would then be lost.

Figure 11:
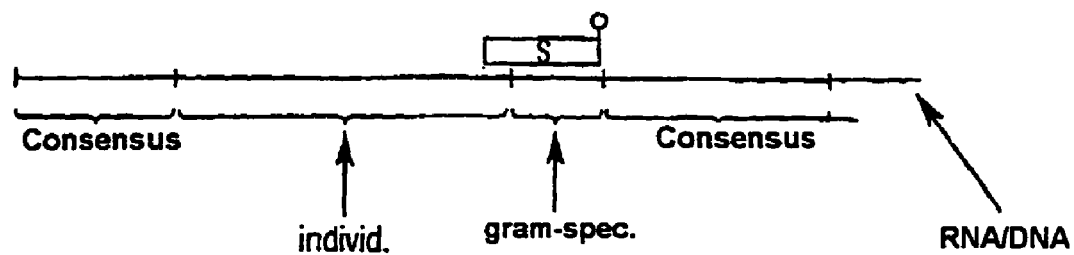
FIG. 11 shows a diagram of the position of primer/probe pairs according to the invention

According to the invention, use is made of consensus primers which flank a highly variant and highly specific region which is suitable for specifically detecting the microorganism (FIG. 11 and FIG. 12). It can be seen from FIG. 12, which depicts an alignment of the corresponding RNA region in different bacteria, how the primers and the Gram (+) probe and the Gram(−) probe are positioned. The distance between the two primers is preferably not too great, between about 100 and 250 base pairs, on the template to be amplified, in order to be able to also amplify incomplete, fragmented DNA/RNA pieces which are present in the sample to be investigated. The primers themselves should not be too long, either, since this can lead to internal loop formation and other steric changes and disturbances which have a detrimental effect on the hybridization properties. In the present case, primers containing from about 16 to about 25 nucleotides were regarded as being appropriate.

It has also been found, surprisingly, that, in practice, it is frequently only DNA/RNA fragments which cannot be amplified by large primers, but which are accessible to amplification by short primers, which are present. However, it is important to find these fragments since this can lead to more rapid and effective treatment being possible. According to one aspect of the invention, the primers are labeled, for example the backward primer is labeled with a dye, such as fluorescein, which is capable of fluorescence transfer, in the region of the last base; as a result, all the amplified nucleic acids contain the label at the consensus region for this primer, with preference in this regard being given to using a fluorescent label which is suitable for FRET, such as fluorescein, which can be bound to thymidine.

A consensus region of the 16S region, which has been mentioned here by way of example, is, for example, 16-20 base pairs in length and extends, in the case of *E. coli*, around bp 350 (see FIG. 12), while the downstream consensus region is located around the base pair 525; the downstream region is followed, seen in the 5' direction, by a distinguishing region which exhibits strong similarities within the Gram(+) bacteria and the Gram(−) bacteria and is about 3 base pairs in length.

Because of internal loop formation, these consensus primers for the 16S region should be between about 16 and about 25 bp in length. The variable, bacterium-specific, region which is located between the highly conserved regions of the primer binding sites is approx. 132 nucleotides in length and its base sequence is highly specific for the genome of different bacterial species.

In a preferred implementation example, those primers which bind to the 16rRNA region of the Gram-bacterium *E. coli* in the region of the conserved bp 341-368 region were designed as forward primers (primer length: 16-18 bases) for bacterial 16rRNA, while the pertinent backward primer binds in the region of the conserved bp 518-535 region (primer length: 16-28 bases). This means that the PCR amplicon is up to about 200 bp in length, preferably shorter.

The consensus primers which were selected, in accordance with the invention, for the 16S region are the primers specified in the sequence listing:

PLK1, as the forward primer, which contains 16-17 bp and binds to base pairs 341-368 in *E. coli*, and PLK2, as the backward primer, which contains 17 bp and binds to base pairs 518-535 in *E. coli*, or the Rev PLK2, which contains 18 bp (1 guanidine longer than PLK2). FOR, containing 19 bp, or PRIMER A, containing 17 bp, are also suitable as forward primers.

On the basis of the above directions, the skilled person is able, at any time, to find other primers which are suitable for highly conserved regions in microbial DNA/RNA, these regions in turn encompassing multivariant regions which can be used for identifying the species. The above primers are only preferred exemplary embodiments for bacteria if the 16s RNA is to be amplified; if the 23s rRNA region is to be amplified, it is then possible to use these directions to select other primers; this also applies to other highly conserved regions of bacterial rRNA, such as 5s RNA. Finally, the "spacer region" between these regions, for example the region at position 1493-1513 of the E. coli 16s rRNA, in the case of an Al primer, and the region at position 23-43 of the E. coli 23s rRNA, in the case of the pertinent B1 primer, as specified by Barry et al. in PCR Methods and Applications, Cold Spring Harbor Laboratory Press, ISSSN 1054-9803/91, pp. 51-56, can also be amplified. Those primers which fit on C. albicans base pairs 544-563 or bp 1033-1014, and amplify parts of the 18ssu rRNA gene sequence, are suitable, for example, in the case of fungi. Another area is that of amplifying and analyzing the topoisomerase II gene, which can also be used for specifying bacterial species (Ragimbeau et al., J Appl Microbiol 1998;85(5):829-838).

Probes

The probes can, in a manner known per se, be designed for the blotting technique and be labeled or unlabeled. Two related probes can be introduced for detecting a group or species; in a special variant of the invention, they are designed such that they bind adjacent to a consensus region and are labeled with a dye which is appropriate for FRET (fluorescence transfer coupling) at the end adjacent to the consensus region.

In connection with this application, highly specific probes are understood as being those probes which correspond precisely to a particular nucleotide sequence in a microorganism and only bind to this template belonging to a single species.

In the context of this application, group-specific probes are understood as being those probes which bind to a group of species possessing common features, for example Gram (+) probes which bind to Gram(+) bacteria since the binding region of the Gram(+) probe possesses nucleotide sequences which correspond with the region to be investigated in the case of Gram+bacteria. These probes are adapted to the region and differ, in a few mismatches, from being a complete fit. The same applies to the fungal probe pair HPA and HPS, which, acting in concert, are capable of FRET, that is, when they bind adjacent to each other, they exhibit the FRET effect by means of fluorescence at 640 nm. HPS and HPA are typical representatives of the 2-probe system, which can likewise be employed in the method according to the invention.

Bacterial probes

Group probes

Figure 10:
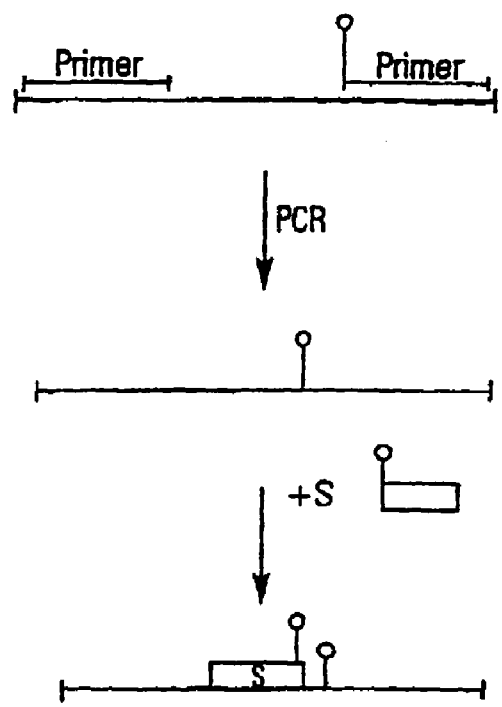
FIG. 10: shows a diagram of the amplification method using a fluorescein-labeled backward primer

As can be seen from FIGS. 10 and 11, at least one of the two abovementioned consensus regions in bacterial 16rRNA is followed, at bp [lacuna] in the case of E. coli, by a Gram(+)/Gram(-) differentiation region which in this case is approx. 3 base pairs in length (Gram-specific region). According to the invention, different probe types are employed.

Probes for the FRET technique are those which are labeled at one end with a dye which is capable of fluorescence transfer, for example RBB 740 or RBB 640 (for example, Light Cycler System—Light. Cycler Instrument—description—Section 6—obtainable from Roche Diagnostics GmbH, Sandhofer Str. 116, D-68305 Mannheim, Germany). If the dye-labeled region of the probe comes into the vicinity of a fluorescence-transferring excitable molecule, for example fluorescein, and if the fluorescein is excited, fluorescence transfer of the excited fluorescein then takes place to a dye which can be excited thereby, for example RBB 740, RBB640 or another dye, which dye then emits. The prerequisite for the fluorescence signal is consequently the spatial proximity between fluorescein and the transfer dye; otherwise, there is no effect. In this connection, the fluorescein can be bound to a second probe (2-probe technique), with it then being necessary, for the effect (fluorescence in a particular wavelength region) to occur, for the two probes to bind to adjacent specific regions.

In connection with this application, highly specific probes are understood as being those probes which correspond precisely to a particular nucleotide sequence in a microorganism and only bind to this template belonging to a single species.

In the context of this application, group-specific probes are understood as being those probes which bind to a group of species possessing common features, for example Gram (+) probes which bind to Gram(+) bacteria since the binding region of the Gram(+) probe possesses nucleotide sequences which correspond with the region to be investigated in the case of Gram+ bacteria. These probes are adapted to the region and differ, in a few mismatches, from being a complete fit.

According to the invention, novel probes have now been developed, which probes enable FRET detection to take place even when the probes are used singly. In that which follows, these probes are termed "single probes".

In this connection, an excitable dye is bound to the last base of the backward primer such that, for example, in connection with an amplification, a fluorescein label at the end of the consensus primer comes to lie on the consensus sequence, corresponding to this primer, of the new RNA at the end of the highly sensitive region. The appropriate probe can now be designed such that it binds to the sequence immediately next to the highly specific region which is circumscribed by the backward primer and is labeled, at its end directed toward the backward primer, with a FRET-excitable dye. Consequently, if the FRET-capable single probe binds in the vicinity of the sequence which is amplified using the labeled consensus primer, it is possible for fluorescence transfer to take place and for the DNA to be detected. As compared with the state of the art, which always required two probes in the highly variable region for the detection, it is only necessary, when using the combination, according to the invention, of fluorescence-capable dye-labeled backward primers and single fluorescence probes, to use a single labeled single probe for detecting the binding of a single probe; the consumption of probes can be substantially reduced.

It is naturally also possible to use probes which are labeled in some other way, for example for the blotting technique, or else probes for the 2-probe technique, if another probe technique is to be carried out (is described below in connection with detecting fungal DNA).

Probes for Gram+ and Gram- Bacteria

It has been found, surprisingly, that relatively short sequence regions which are common to the Gram+ and Gram- bacteria also occur in the highly variable region between the two 16srRNA primer sequences. Probes for one of these two groups consequently have to possess the specific analogous sequence which is common to the microorganism group which is to be detected. If, for example, the identification is to be carried out by way of the 16RNA region in the case of Gram-negative bacteria, the following probes according to the invention are then suitable, for example:

Typical single probes for the 16 S RNA of Gram-positive bacteria are: ISP2 containing 30 bases or ISP containing 24 bases Typical single probes for Gram-negative probes ISN2 containing 28 bases or ISN containing 23 bases.

For example, the single probes ISN2, which are group-specific for Gram-negative bacteria, and which have the sequence, in the 5'-3' direction, of accgcagaataagcaccg-gctaacgtgc X, where X=LC640, bind to the bp 467-497 region of the *E. coli* 16rRNA gene, which region on the 16sRNA gene is the same in the case of essentially all Gram-negative bacteria. Single probes for Gram+ bacteria bind to bp [lacuna] in *E. coli*.

The group-specific single probes for finding Gram+ bacteria, i.e. ISP2*, binds to the bp 467-497 region of the *E. coli* 16rRNA gene, which region on the 16sRNA gene is the same in the case of essentially all Gram-negative bacteria.

Both the probes must be used with a backward primer, such as PLK2*, which ends at bp 517 in *E. coli* and is labeled with fluorescein in this region.

The group-specific probes which are used here have been extended beyond the common sequence of the group or exhibit a few mismatches, preferably 1-4 and particularly preferably 1-3 in the case of a probe length of approx. 25-30 bp, such that different numbers of mismatches occur in the case of different bacteria in the microorganism group. These mismatches can then be detected, inter alia, by the hybrids obtained with the DNA amplificates having different melting points and melting curves, thereby enabling the bacterial RNA which is present to be differentiated.

Other examples of organism-specific probes and consensus primers can, with the invention being in no way restricted to these probes and primers, are the oligonucleotides listed below:

List 1

Base sequences, in the 5' to 3' direction, of examples of oligonucleotides which can be used as probes and primers:

| Nucleot. | Organism | Sequence (5'-3' direction) | |
|---|---|---|---|
| specific probes, bacteria | | | |
| SLK 1 | E. coli | agggagtaaagttaatacctttgctc | (SEQ ID NO: 11) |
| SLK 2 | Staph. epi | gaacaaatgtgtaagtaactatgcacg | (SEQ ID NO: 12) |
| SLK 3 | Pseudomonas | ggaagggcagtaagttaataccttg | (SEQ ID NO: 13) |
| SLK 4 | Acinobacter baumannii | atacctagagatagtggacgttactc | (SEQ ID NO: 14) |
| SLK 5 | Staph. aureus | gaacatatgtgtaagtaactgtgcaca | (SEQ ID NO: 15) |
| SLK 6 | Enterococcus faeciumn | gatgagagtaactgttcatcccttg | (SEQ ID NO: 16) |
| SLK 7 | Enterococcus faecialis | gacgttagtaactgaacgtcccct | (SEQ ID NO: 17) |
| SLK 8 | Haemophilus influ. | tgatgtgttaatagcacatcaaattgac | (SEQ ID NO: 18) |
| SLK 9 | Enterobacter cloacae | gacagggttaataaccctgtcgatt | (SEQ ID NO: 19) |
| SLK 10 | Klebsiella pneumoniae | cgatgaggttaataacctcatcgatt | (SEQ ID NO: 20) |
| SLK 11 | Serratia | aatacgctcatcaattgacgttactc | (SEQ ID NO: 21) |
| SLK 12 | Legionella pneu. | ggttgataggttaagagctgattaac | (SEQ ID NO: 22) |
| SLK 13 | Proteus vulgaris | tgataaagttaatacctttgtcaattgac | (SEQ ID NO: 23) |
| SLK 14 | Bacteroides fragiles | tgcagtatgtatactgttttgtatgtatt | (SEQ ID NO: 24) |
| SLK 15 | Streptococcus pyogenes | gtgggagtggaaaatccaccaagt | (SEQ ID NO: 25) |
| SLK 16 | Mycobact. pneum. | gtaatggctagagtttgactgtacca | (SEQ ID NO: 26) |
| SLK 17 | Corynebact. Jejuni | cactgtgtggtgacggtacctg | (SEQ ID NO: 27) |
| SLK 18 | Enterobacter aerog | accttggcgattgacgttactcgc | (SEQ ID NO: 28) |
| SLK 19 | Mycobact. tuberculosis | ctctcggattgacggtaggtggag | (SEQ ID NO: 29) |
| group-spec. probes, bacteria (gram+/gram-) | | | |
| SKNI | Gram(-) probe | gaggcagcagtggggaatattg | (SEQ ID NO: 30) |
| ISN2 | Gram(-) probe | accgcagaataagcaccggctaactccgtgcX, where X = LC640 | (SEQ ID NO: 43) |

-continued

| Nucleot. | Organism | Sequence (5'-3' direction) | |
|---|---|---|---|
| ISN2* | Gram(-) probe | ccgcagaataagcaccggctaactccgtX where X = LC640 | (SEQ ID NO: 44) |
| ISN | Gram(-) probe | agaagcaccggctaactccgXtgc | (SEQ ID NO: 34) |
| SKPI | Gram-positive probe | gaggcagcagtagggaatcttc | (SEQ ID NO: 31) |
| ISP2* | Gram-positive probe, labeled | cctaaccagaaagccacggctaactacgtg X, where X = LC705 | (SEQ ID NO: 45) |
| ISP2 | Gram-positive probe, labeled | cctaatcagaaagcgacggctaactacgtgcX where X = LC705 | (SEQ ID NO: 46) |
| ISP | Gram-positive probe, labeled | agaaagccacggctaactacgXtgc where X = LC705 | (SEQ ID NO: 33) |
| Forward primers, bacteria, 16rRNA: | | | |
| PLK1H | | tacgggaggcagcagt | (SEQ ID NO: 5) |
| FOR | | tcctacgggaggcagcagt | (SEQ ID NO: 4) |
| PLK1 | | ctacgggaggcagcagt | (SEQ ID NO: 3) |
| AR3: | | gcg gtg aaa tgc gta gag at | (SEQ ID NO: 9) |
| Backward primers, bacteria, 16 rRNA: | | | |
| PLK2H | | tattaccgcggctgctX | (SEQ ID NO: 47) |
| REV iFL, labeled | | gtattaccgcggctgcXtg | (SEQ ID NO: 2) |
| Primer iFL | | tattaccgcggctgcXtg, where X = fluorescein, | (SEQ ID NO: 1) |
| AR4: | | gtt tac ggc gtggactacca | (SEQ ID NO: 10) |
| Forward primers, fungi: | | | |
| PFUI fungal consensus primer | | attggagggcaagtctggtg | (SEQ ID NO: 7) |
| Backward primers, fungi: | | | |
| PFU2 fungal consensus primer | | ccgatccctagtcggcatag | (SEQ ID NO: 8) |
| Probes for fungi: specific probes: | | | |
| ScaI | Candida albicans | tctgggtagccatttatggcgaaccaggac | (SEQ ID NO: 35) |
| SCKI | Candida krusei | gtctttccttctggctagcctcgggcgaac | (SEQ ID NO: 36) |
| SCPI | Candida parapsilosis | tttccttctggctagcctttttggcgaacc | (SEQ ID NO: 37) |
| SctI | Candida tropiealis | gttggccggtccatctttctgatgcgtact | (SEQ ID NO: 38) |
| Stg 1 | Torulopsis glabrata | ttctggctaaccccaagtccttgtggcttg | (SEQ ID NO: 39) |
| SAUI | Aspergillus | catggccttcactggctgtgggggaacca | (SEQ ID NO: 40) |
| group-spec, probes: | | | |
| HPA | general fungal probe 1 | ctgaatgattaatagggacggtcgg-fluorescein | (SEQ ID NO: 41) |
| HPS | general fungal probe 2 | LC640-ggtatcagtattcagttgtcagaggtgaaa | (SEQ ID NO: 42) |

While the invention can be realized using the above-listed oligonucleotides, it is in no way restricted to the microorganisms and nucleotides which are listed above by way of example but, as is evident to the skilled person, can also be applied, mutatis mutandis, to other microorganisms using other nucleotides.

FIGS. 2, 3 and 4 depict possibilities which ensue from using oligonucleotide probes in the PCR. These probes are specific, novel probes: ISN1 for Gram-negative bacteria and the group-specific probe ISP for Gram-positive bacteria. *E. coli* DNA and *Staph. epidermidis* DNA are shown as examples. While the Gram-negative probe only gives a signal with *E. coli* in the PCR, this probe does not give any signal in the case of the sample containing *Staph. epi.* DNA (upper part of FIG. 2). Conversely, while the oligonucleotide probe for Gram-positive bacteria identifies the gram+ *Staph. epi* unambiguously, it is negative for the sample containing *E. coli* DNA.

FIG. 3 and FIG. 4 depict the melting curve analysis for the same probes. An unambiguous differentiation using the oligonucleotides can also be performed with the aid of the melting curves. In addition to this, it is also possible to carry out further differentiation within the Gram-negative bacteria using the melting curve analysis performed on the probe for Gram-negative bacteria.

FIG. 5 shows that a markedly lower melting temperature than that obtained when the probe matches completely (*Enterobacter aerogenae* and *Serratia marcescens*) is already obtained when there is one (n=1) mismatch (*Pseudomonas aeruginosa*).

The invention will be explained in more detail below with the aid of implementation examples.

A. Identifying Microorganisms Qualitatively

EXAMPLE 1

Isolating the DNA from whole blood:

In order to isolate the free bacterial DNA from patient plasma, whole blood is collected in an EDTA whole-blood tube (3.2 ml; Sarstedt). After having been withdrawn, the whole blood is immediately centrifuged at 2000 g for 3 min. The plasma, forming the supernatant, is carefully drawn off from the cellular components. The plasma is either subjected directly to further processing or stored at −25° C.

All the DNA preparations are carried out using the "High Pure viral Nucleic Acid Kit" nucleic acid isolation kit supplied by Roche Molecular Biochemicals. The centrifugation steps are carried out in a Heraeus centrifuge. An Eppendorf thermomixer is available for the incubations. Eppendorf pipettes are used in the work. All the pipette tips are autoclaved and fitted with filters. (The principle is described by Vogelstein, B. and Gilles in D. Proc. Natl. Sci. USA 76, 615-619, the entirety of which is hereby incorporated by reference.).

The following standard protocol is used for isolating DNA from 200 µl of plasma: 200 µl of binding buffer (6M guanidinium chloride, 10 mmol of urea, 10 mM Tris-HCl, 20% Triton X-100(v/v) in 25 ml, pH 4.4 (25° C.)) and 40 µl of proteinase K solution (90 mg of lyophilized proteinase K+4.5 ml of double-distilled H2O) are mixed with 250 µl of plasma in a 1.5 ml Eppendorf tube and the mixture is incubated at 72° C. for 10 min. 100 µl of isopropanol are then added to the sample which has been treated in this way and the whole is thoroughly mixed. The sample is pipetted into the upper reservoir of the High Pure filter tube and centrifuged at 8000×g for 1 min. The step of washing with i-propanol is repeated. The nucleic acids which are bound in the tube are eluted, likewise at 8000×g for 1 min, using 50 µl of elution buffer. The DNA solution contained in the collecting vessel is either stored at −25° C. or used immediately for the PCR.

Decontaminating the Mastermix:

The 16 S RNA is a highly conserved region within the bacterial genome and is therefore very well suited for the general detection of microbial DNA by means of a polymerase chain reaction (PCR). However, contaminating bacterial DNA from recombinantly prepared reagents is also concomitantly amplified and leads to "background noise" in the method, due to the contaminating microbial DNA being amplified.

Because all commercial Taq polymerases are prepared recombinantly in a bacterial host, and the enzyme is insufficiently purified, the Taq polymerase is itself the main source of contamination with microbial genomic DNA. It is necessary to decontaminate the polymerase, and the mastermix, which contains the reagents which are essential for the PCR, before the template DNA is added in order to reduce what is termed the background noise of the method.

Unless otherwise indicated, all the following reagents are derived from the SYBR Green 1 kit (Roche). Preparing the mastermix for the decontamination in a sterile 1.5 ml Eppendorf tube:

9.4 µl of double-distilled H2O)

2.4 µl of MgCl2-stock solution)

2.0 µl of CYBR Green 1 mastermix)

0.2 µl (corresp. to 1 unit) of enzyme Mbo 1 (New England Biolabs)

The mixture is briefly vortexed and centrifuged (13000 g, 10 s). There then follow 45 min of incubation at 37° C., during which the restriction enzyme cuts contaminating bacterial template, which can thus no longer be amplified in the subsequent PCR. After this decontamination, the restriction endonuclease is inactivated for 3 min at 95° C. and the mixture is then cooled on ice. After that, 0.5 µl (corresp. to 10 pmol) of each of the PCR primers AR3 and AR4, which do not enclose any hypervariable region, are added. The primers which are used here are obtained from Biomol (Belgium) and purified by HPLC.

The primer sequences are as follows:

Forward: AR3: 5'-gcg gtg aaa tgc gta gag at-3' (SEQ ID NO: 9)

Backward: AR4: 5'-gtt tac ggc gtg gac tac ca-3' (SEQ ID NO: 10)

The mastermix is subsequently briefly vortexed and centrifuged (13000 g, 10 s). After that, 15 µl of the decontaminated mastermix is transferred into the LightCycler capillary and 5 µl of sample DNA (or standard dilution samples, Sau.) are added. After that, the capillaries are sealed, centrifuged at 1000 g for 10 sec, and inserted into the LightCycler rotor.

EXAMPLE 2

Preparing a patient sample (BAL)

A bronchioalvaeolar lavage (BAL) using water—this means that water is introduced, using a bronchoscope, into the lung, for rinsing, and then aspirated once again—was prepared. For this, 200 µl of BAL were worked up using the ROCHE High Pure Viral Nucleic Acid Kit—i.e. they are treated with 200 µl of working solution, consisting of 200 µl of binding buffer (6M quanidinium chloride, 10 mmol of urea, 10 mM Tris-HCl, 20% TRITON X-100 (octyl phenol ethoxylate) (v/v) in 25 ml, pH 4.4 (25° C.)), in which 2 mg of poly(A) carrier RNA lyophilisate are dissolved, and then treated with 40 µl of proteinase K solution (90 mg of lyophilized proteinase K+4.5 ml of double-distilled H2O). After the aqueous proteinase K solution has been added, the whole is thoroughly mixed immediately and incubated at 72° C. for 10 min. After incubation, the samples are treated with 100 µl of analytical-grade isopropanol and mixed thoroughly. A high pure filter tube containing a specially prepared glass material—polypropylene tubes having a capacity of up to 700 µl sample volume and which contain a glass fiber mat—is now inserted into a 2 ml polypropylene collecting vessel and the sample is pipetted into the upper reservoir. The collecting vessel, together with filter tube and sample, is centrifuged at 8000×g for 1 min in a standard bench centrifuge. The flowthrough which emerges from the filter tube is discarded; the DNA remains bound in the filter tube. The filter tube is inserted into a new collecting vessel. The DNA which is bound to it is washed with 450 µl of washing buffer (20 mM NaCl, 20 mM Tris-HCl, pH 7.5 (25° C.) in 40 ml of analytical-grade abs. ethanol+10 ml of water), which is pipetted into the upper reservoir and pressed through the tube by the latter being centrifuged at 8000×g for 1 min. This washing step is repeated with 450 µl of washing buffer in a new collecting vessel, with centrifugation now being carried out at the max. speed of the centrifuge, i.e. approx. 13000×g, for 10 s after the centrifugation at 8000 g has been concluded.

After that, the collecting vessel is discarded and the washed filter tube is inserted into a new, nuclase-free 1.5 ml reaction vessel. In order to elute the nucleic acids from the glass surface, 50 µl of elution buffer (nuclease-free double-distilled H2O) which has been heated to 70° C.) are now pipetted into the filter tube and the whole is centrifuged at 8000×g for 1 min. The nucleic acid solution which emerges is immediately subjected to further processing in the PCR (or stored at 2-8° C. for subsequent analyses).

However, the nucleic acids can be isolated using any other suitable method, for example using the MAGNA-Pure appliance supplied by ROCHE, which enables nucleic acids to be extracted from solutions in an automated manner and thereby avoids errors which could arise as a result of sampling/processing which is not automated. The isolation of fungal DNA from whole blood is described, for example, in WO 97/07238, the entire disclosure of which is hereby incorporated by reference.

EXAMPLE 3

Amplifying the isolated bacterial nucleic acids using labeled consensus primers and labeled gram+-specific and gram--specific probes 2 µl of mastermix, 2 µl of Fast Start Mix f. hybprobes-Roche, 2.4 µl of 25 mM MgCl2 in H2O, 10 pmol of PLK 1 primer and 8 pmol of the fluorescence-labeled backward primer IFL are in each case added to 2 µl of sample solution containing *Bacteroides fragilis, Pseudomonas aeruginosa, Escherichia Coli* and *Klebsiella pneumoniae*. The IFL primer is labeled with fluorescein on its penultimate thymidine base such that the amplified DNA always contains a fluorescein label which is incorporated close to the specific region of the 16S region. The Roche FastStart Mix is preferably used for PCR. 3 pmol of the gram(+) probe ISP2, which is labeled with LC705 on its last guanidine, and 3 pmol of the gram(-) probe ISN2, which is labeled with LC640 on the thymidine at the 3' end, are added and the mixture is diluted with dist., highly pure H2O to 18 µl.

Mastermix and sample are combined, aliquoted into the PCR capillaries of a Light-Cycler, and centrifuged down into the capillary by centrifugation in a laboratory centrifuge at 800×g for 1 min. The capillary is then inserted in the Light Cycler and 45 cycles are run between 95 and 52° C.

After the amplification, and as a conclusion to the PCR in the Light Cycler, a PCR melting curve is determined while analyzing in the 640 nm channel. The melting curves of the different bacterial DNAs are depicted in FIG. 6. FIG. 6 shows that measuring in the 640 nm channel gives the amplification products which are specifically detected by the Gram-negative probe, or the hybridization product between this probe and the bacterial RNA, with each different Gram (-) organism giving a different melting curve. Bacterial DNA from Gram(+) bacteria in the same sample can be measured in the 750 nm window when labeling with the Gram(+) probe. Use of the differently labeled probes makes it possible to use 2 probes to detect Gram(+) and Gram(-) bacteria in a sample and to differentiate them on the basis of the melting point.

It can be clearly seen in FIG. 6 that the probe gives different melting curves with different bacterial RNAs, with it being possible to explain the different melting curves on the basis of the mismatches between the probe and the DNA. The differences obtained in the melting curve forms using Gram(-) bacterial DNA make it possible to identify the bacterium which was present in the sample solution in a rather precise manner. In the present case, a first melting curve occurs in the range 40-55° C.; i.e. the probe melts off the Bacteroides amplificate (Bacteroides) at an early stage, with this being followed, as the next bacterium, by *Pseudomonas*, which has a second, very broad melting curve in the 45-65° C. region. By combining the melting curve analyses, it is possible, in this case, to differentiate the organisms of different bacterial species still further without any additional PCR, or any opening of the capillary for the purpose of adding another reagent, being necessary.

EXAMPLE 4

Detecting several bacterial species from pure-culture strains alongside each other A 1:4 mixture of *Pseudomonas* and *Staph. epidermidis* was prepared and amplified in the presence of the ISP2 probes, as indicated in the previous example. The melting curve in FIG. 7 shows clearly that ISP2 is only able to recognise *Staph. epi*. and that *Pseudomonas* does not interfere with the signal from *Staph. epi*. A comparable conclusion ensues from FIG. 8, where the same experiment was carried out using ISN2; in this case, it is only the Gram(-) microorganism *Pseudomonas* which is detected, with *staph. epi*. evidently not interfering with the detection.

It is consequently possible to detect different species alongside each other in one measurement.

EXAMPLE 5

Detecting fungal DNA from pure-culture strains

Probes/primer combinations which can be used specifically for amplifying/detecting fungal DNA are given in list 1. The method is carried out in an analogous manner to that for detecting the bacteria.

EXAMPLE 6

Detecting and identifying bacterial rRNA from patient samples

In each case 3 ml of a bronchioalvaeolar lavage (BAL) using water (this means that water is introduced, by way of a bronchoscope, into the lung, for rinsing, and is then aspirated once again), which lavage was in each case obtained from two intensive-care patients P2 and P4 who were suffering from lung problems, were diluted 1:50 with double-distilled water. For information, it may be added that there are no organisms in a BAL obtained from healthy subjects.

The BAL fluid which had been diluted in this way was purified using the High Pure Viral Nucleic Acid kit, as indicated in Example 2.

After that, the sample which had been prepared in this way was aliquoted into different capillaries:

Each sample was amplified in the LightCycler, using consensus primers PLK1 and PLK2 in the presence of SYBR Green, and the fluorescence of the double-stranded amplificates, and their melting behavior, was then investigated, after 40 cycles, in the SYBR-Green format. The result is depicted in FIG. 1b.

As can be seen by comparing with FIG. 1, the melting point of the amplified double-stranded DNA part of P4 which was stained with SYBR Green is identical to that which was measured using a pure culture of *Pseudomonas aeruginosa* (ATCC 27852); it is in the same region as *Enterococcus faecalis, Streptococcus pneum.* and *staph epidermidis*; by means of the PCR/SYBR-Green analysis, it was possible to restrict the possible microorganisms to a few organisms which had to be tested. A comparison with the results of the microbiology, which was able to detect this organism several days after taking the sample, confirmed the results of the PCR/melting point analysis, which was available within one hour.

The sample from patient P2 was likewise amplified with the consensus primers PLK1 and PLK2 and the melting point of the double-stranded product which was formed was then investigated using SYBR-Green; the melting point of the amplified product corresponds to that of *Enterobacter cloacae* and *Serratia marcescens*, as can be seen from FIG. 1; the microbiological investigation demonstrated that it was *Enterobacter cloacae* which was present.

Accordingly, it was possible, within one hour, by means of the method according to the invention, to greatly limit, in the Hyb-probe format, the number of possible microorganisms which in fact had to be specifically tested, with it then being possible to precisely identify the microorganism, for example using specific probes, within a further hour, and a therapy which is geared toward the microorganism can then begin rapidly and effectively.

Figure 9:
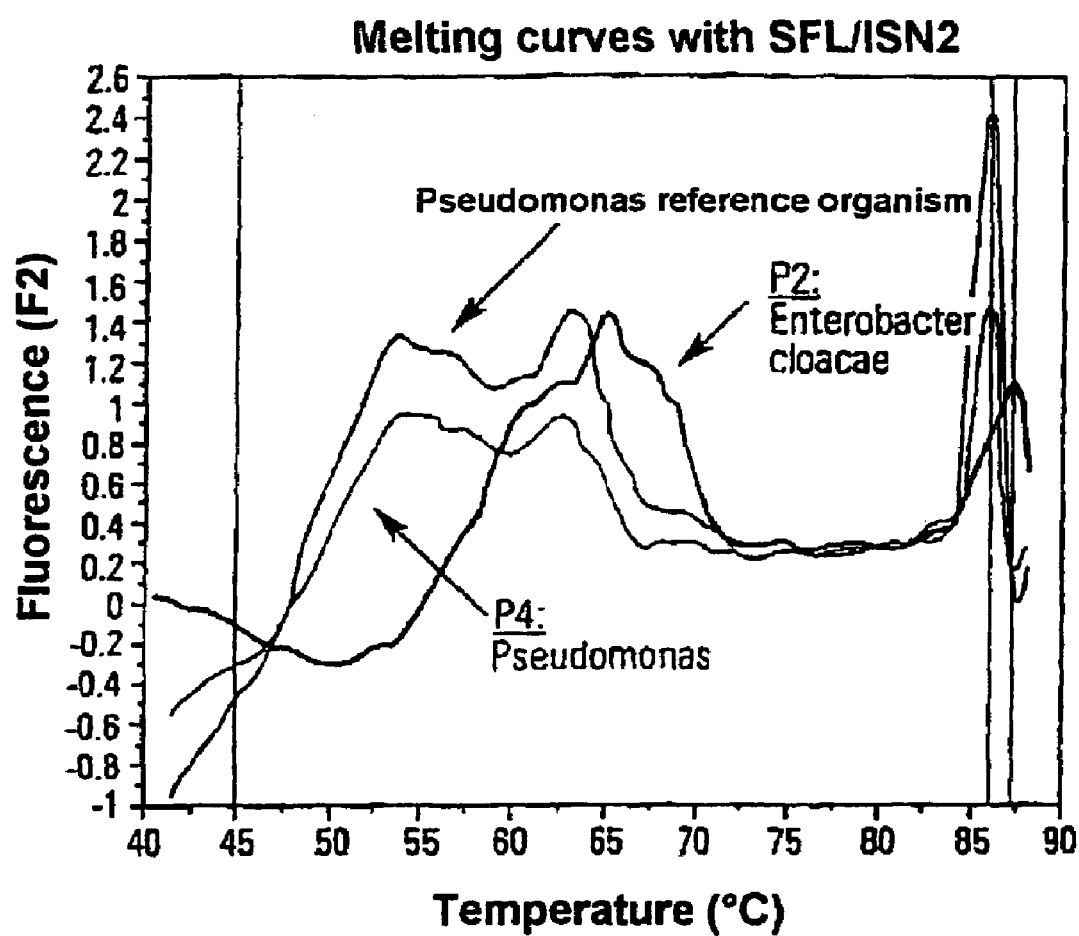
FIG. 9 shows melting curves of BAL patient samples (P2 and P4) in the hybridization probe format with ISN2

The same BAL samples from P4 and P2 were also treated with the consensus primers PLK1 and PLK2 and the probe pair ISN2/ISP2 and investigated after the PCR amplification in the Light-Cycler. The result of the melting point analysis of the hybridization product with ISN2/ISP2 is depicted in FIG. 9. In this case too, it is clearly seen that, in the case of P4, it is only possible to measure a fluorescence of the ISN2 probe (fluoresces at 640 nm)—with the shape of the curve corresponding to that of *Pseudomonas* with the ISN2 probe, as is evident from a comparison with the curve obtained using the pure-culture organism as shown in the same FIG. 9 and in FIG. 6. This made it appear probable that *Pseudomonas* was present. This is also indicated by the melting point. It is consequently possible to use the ISN2 probe to only find Gram-negative bacteria, that is to exclude the gram(+) bacteria, and then to restrict the choice even more narrowly on the basis of the special melting points of the hybridization product or, in many cases, already to identify the microorganism directly in this run.

The P2 sample exhibited a curve shape which resembled that of *Enterobacter cloacae*; in fact, the microbiology was once again able to confirm the presence of this organism.

It is consequently possible, according to the invention, to already make a preliminary choice, in the SYBR-Green format and by way of determining the melting points of the amplified product, of organisms which may possibly be present; in the probe format, it is possible to use group-specific probes to make narrower distinctions between possible microorganisms within a very short period of time.

The microorganism could then be identified, using specific probes and their melting point, in a further PCR, as is known, for example, from the Light-Cycler system and the directions for the Light-Cycler instrument. However, the method according to the invention makes it possible to greatly limit the number of experiments which in fact have to be carried out using specific probes, or, in the case of many organisms, whose melting curves have a shape which is so typical that no other melting curve has this shape, makes it possible to avoid any further identification at all.

B. Quantifying the DNA:

In many cases, it is desirable to be able to establish whether the organism burden in the original sample was high, and consequently pointed to an acute infection, or whether it was instead low, that is indicated an infection which had subsided or an infection which was just beginning. It is also necessary to establish whether this organism load could possibly represent normal colonization or whether this colonization with microorganisms is pathogenic. In order to establish these points, it is necessary to prepare an appropriate comparison standard.

Preparing a Standard Dilution Series:

In order to determine bacterial genomic DNA quantitatively, it is necessary to prepare a standard dilution series using known concentrations of template DNA, which is concomitantly amplified in each PCR. The (Roche) Light-Cycler calculates a regression curve from the fluorescence of the standard dilution samples, with this curve then being used to calculate the concentrations of the samples.

For the standard dilution series, genomic DNA from staphylococcus epidermidis was quantified photometrically at 260 nm. In this connection, an optical density (OD) of 1.0 corresponds to 50 µl of double-stranded DNA/ml. The purity of the samples is ascertained from the OD(260):OD(280) ratio. A ratio of 1.8-2.0 is regarded as being pure. The DNA is then diluted to 500, 100, 50, 10, 5 and 1 fg/µl. 5 µl of each of these dilutions were added, as a template, to the PCR mastermix.

Preparing a Plasmid Standard

It has emerged that a genomic standard is not always optimal for the amplification since, because of the presence of side chains which are methylated to different extents, it is not possible to obtain an amplification which is completely uniform. For this reason, a plasmid standard was evolved.

A PLK product (180 base pairs), that is a product which is amplified by the two PLK primers, is cloned into the Invitrogen vector pCR(r)4TOPO(r) using the TOPO TA cloning kit for sequencing, with the resultant vector being transformed into the bacteria contained in this kit, and amplified in this bacteria, and then isolated from the bacteria and quantified (photometrically at OD 260 nm: 1=50

µg/ml)—see Maniatis or else Shuman, S. (1994), J. Bio. Chem. 269, 32678-32684 and Bernard, P. et al. (1993) J. Mol. Bio. 234,534-541)

The quantification can also be effected using any other suitable method, for example using SYBR Green in accordance with the method of the FHG [Fraunhofer Gesellschaft] for interfacial research, Stuttgart, Germany. The quantified product is diluted and used with water for the calibration curve.

Polymerase Chain Reaction (PCR):

The PCR is carried out on a LightCycler (Roche) using the Lightcycler Run Software 3.39. An initial denaturation was first of all carried out at 95° C. for 30 sec using a 20°/sec transition rate. This was then followed by 45 cycles of:

denaturation, 95° C., 1 sec, 20° C./sec annealing, 60° C., 5 sec, 20°/sec extension, 72° C., 7 sec, 20°/sec measurement, 83° C., 0 sec, 20°/sec, (acquisition mode: single).

Following the amplification, the resulting product is analyzed by means of a melting curve. The conditions for this are as follows:

denaturation, 95° C., 3 sec, 20° C./sec cooling, 60° C., 30 sec, 20°/sec measurement, 95° C., 0 sec, 0.1° C./sec, acquisition mode: continuous In conclusion, the PCR was terminated by means of a cooling step of 40° C., 30 sec. 20°/sec.

Data Analysis/Quantification

The semiautomated Lightcycler software 3.1.102 is used for the data analysis and quantification of the bacterial DNA. The analysis and quantification take place in three steps and are predetermined by the software:
1. Establishing the autofluorescence threshold using software in the arrhythmetic mode
2. Establishing the noise band manually using the curves of the standard dilution series. The noise band is placed in the log-linear part of the standard dilution series immediately after the lower inflection point.
3. Quantifying the samples using a regression curve which is calculated from the standard dilution series using the LightCycler software.

EXAMPLE 7

Using the blotting technique/PCR to determine bacterial DNA in plasma from sepsis patients The same procedural steps as in Example 2 were carried out, but using plasma from sepsis patients; however, the PCR reagents were decontaminated in the following manner:

Purification Methods

Since the polymerases which are used for the PCR are mostly of bacterial origin and therefore frequently contaminated with bacterial DNA, it is as a rule necessary to eliminate the contamination prior to the nonspecific PCR in order to prevent decontaminating DNA from being concomitantly amplified and in this way leading to a falsely positive result. It is therefore useful to employ highly pure polymerase or, if this polymerase does not meet the requirements, to decontaminate the polymerase which is used in the PCR amplification before employing it to amplify the microbial DNA/RNA, for example by treating with a restriction enzyme, by means of methoxypsoralen/UV irradiation, or by means of other suitable methods.

Purifying the Bacterial PCR Reagents by Means of Methoxypsoralen Treatment

While it is appropriate to quantify microbial DNA/RNA by means of PCR amplification, the contamination of the PCR reagents with microbial DNA constitutes a serious problem which leads to falsely positive results when a universal 16S rRNA primer is used. In this case, 8-methoxypsoralen, combined with UV irradiation, is used to inactivate the contaminating DNA.

The effect of 8-methoxypsoralen on the PCR agents, in particular on the background noise of contaminating 16S rRNA, is investigated using a real-time PCR system for detecting microbial DNA in the plasma of sepsis patients. In this case, too, all the PCR reactions were once again carried out on the Lightcycler instrument (Roche). Quantification was carried out in accordance with the SBYR Green I method. 25 µg of 8-methoxypsoralen/ml (8-methoxy-psoralen supplied by Sigma Corporation), and UV irradiation (366 nm) for 5 min, were used for the decontamination. The 8-methoxypsoralen was dissolved in 2.5% dimethyl sulfoxide. As a result of the PCR agents having been decontaminated, it is now possible to use the melting curve analysis to distinguish 16S rRNA from amplified Staphylococcus epidermidis DNA (melting point of the contaminating E. coli DNA 89° C.; melting point of the Staphylococcus epidermidis DNA: 87° C.). Treatment of the PCR reagents with 8-methoxypsoralen and UV irradiation resulted in up to 800 copies of bacterial DNA being eliminated, with it being possible to amplify 400 copies, which were added to a sample after the decontamination procedure, without the contaminating DNA being coamplified.

Treatment of the PCR reagents with 8-methoxypsoralen and UV accordingly leads to a satisfactory elimination of contaminating microbial DNA. The remaining steps were carried out as described in Example 1.

EXAMPLE 8

While the methods were carried out as described in Example 1, the PCR agents were decontaminated as follows:

Purifying the PCR Agents with DNAse

An alternative method of purifying the PCR reagents is that of using DNAse. In order to purify the PCR agents which lead to falsely positive results in a real-time PCR, and which are derived from microbial DNA during the preparation of the PCR reagents, the PCR reagents are treated with DNAse for 15 min. After that, the DNAse was inactivated by heat treatment at 95° C. for a period of 50 min. Deep-Vent-Exo(-) polymerase and Ampli-Taq polymerase were employed for the polymerase chain reaction amplification using broad-band primers composed of conserved microbial 16S ribosomal DNA nucleotide sequences. The PCR agents which had been decontaminated in this way made it possible to exclude the contaminating bacterial DNA from the PCR reagents.

Using the PCR reagents which had been purified in accordance with the invention, it was possible to determine bacterial DNA concentrations of only 6 pg/ml.

EXAMPLE 9

Rough identification of bacterial DNA using the DNA melting curves for different bacteria (SYBR-Green)

The Gram-negative bacteria exhibited a melting temperature of between 89.7 and 89.1° C., whereas the Gram-positive bacteria exhibited a melting temperature of between 87.9 and 87.6° C. *E. coli* exhibits the same melting temperature as the DNA contaminating the Taq polymerase. This indicates that the contaminating DNA originates from *E. coli*-derived polymerases. In the present case, amplification products obtained from patients suffering from sepsis exhibited melting curves which differed from this background signal. These curves exhibited melting temperatures of 88.1 and 87.2° C. The identification of the bacteria can be refined by hybridizing fluorescence dye-labeled oligonucleotides to the amplified bacterial DNA.

Accordingly, DNA melting point analysis combined with the hybridization of specific, fluorescence dye-coupled oligonucleotides to the PCR product, is an adequate method for very rapidly distinguishing and identifying bacterial species.

Identifying Bacteria by Combining PCR in the Presence of Different Polyspecific Hybridization Probes Detecting *E. coli*

A PCR was carried out, in the Roche LightCycler and over 45 cycles, on *E. coli* genomic DNA using the PLK1 primer and the fluorescein-labeled IFL primer in the presence of the RRC-labeled ISN2 probes. After the cycles had been concluded, a melting curve was performed on the hybridized products of the amplified bacterial DNA. A melting curve of the hybridization product with the probe for gram-bacteria was found at the 705 nm wavelength, indicating that the DNA of a Gram-negative bacterium was present. In this case, the maximum of the df/dt curve, i.e. the melting point range of the hybridization product of *E. coli* with the ISN2 probe, was between about 52 and 66° C.

The same melting curve study at 640 did not show any melting curve; i.e. the gram(+) probe had not found any DNA from Gram-positive bacteria and did not therefore furnish any signal (see FIG. 6)

Detecting *Staph. epidermidis*

The same experiment as under 1 was carried out using *staph. epi* DNA. The hybridization product with the gram(+) probe ISP2 was found to have a melting range of between 50 and 64° C. (see FIG. 7). Since no DNA from Gram-negative bacteria was present, the gram(-) probe ISN2 did not give any signal.

It is, of course, always possible, after a preliminary classification of this nature, to verify the choice once again by means of hybridizing with a species-specific probe, in order to increase the reliability of the method.

Specifying the Amplified PCR Products

An example of the identification of the organism species which is carried out in the second step of the method is the technique of the reverse dot blot. Specification of the organisms is not restricted to this technique but can also be performed, for example, by means of the DNA microchip technique.

EXAMPLE 10

Specifying the amplified DNA/RNA by means of reverse dot blotting:

Specific probes were used to identify various microorganisms, i.e. *Candida albicans; Candida krusei; Candida parapsilosis; Candida tropiealis; Torulopsis glabrata; Aspergillus; E. coli Staph. epi; Pseudomonas, Acinobascter baumanii; Staph. Aureus; Enterococcus faecium; Enterococcus faecialis; Haemophilus infu.; Enterobacter cloacae; Klebsiella pneumoniae; Serratia; Legionella pneu. Proteus vulgaris; Bacteroides fragilis; Streptococcus pyogenes; Mycobact. pneum.; Corynebact. Jejuni; Enterobacter aerog.* and *Mycobact. tuberculosis*, as can be seen in list 1, after their DNA/RNA had been amplified.

The PCR product of the reaction for quantifying bacterial DNA is labeled, during the PCR reaction, by incorporating digoxigenin-labeled dUTP (fungal DNA is amplified using the consensus primers PFU1 and PFU2, as specified in list 1). After it has been quantified by means of real-time PCR, the PCR product is used for hybridizing to an organism-specific oligonucleotide probe which has been fixed on a positively charged nylon membrane (reverse dot blot). The positive binding of the PCR product to a specific probe (probe design for the bacterial species and fungal species: see list 1) can be detected by means of a chemiluminescence signal on a X-ray film, after binding an antibody and after a substrate reaction.

Materials Required:
  Falcon tubes (50/25 ml);
  Nylon membrane (for example Roche Diagnostics) (approx. 5×8 cm$^2$).
  2 μl each of the corresponding oligonucleotide probes, at a concentration of 100 pmol/μl, and the PCR product, which was labeled by incorporating Dig-dUTP (positive control for the detection), were applied to the dry nylon membrane. The nucleic acids were fixed on the nylon membrane by irradiating with UV (crosslinking with UV light (302 nm, 400 mJoule/cm$^2$)).

Prehybridization: (1 hour)
  30 ml of standard hybridization buffer were introduced into Falcon tubes, after which the membrane was inserted and the tubes were incubated at hybridization temperature (50° C.) for 1 hour.

Hybridization: (1 hour)
  The DNA of the Dig-dUTP-labeled PCR product to be specified was heat-denatured at 95° C. for 10 min and then cooled on ice. If the frozen (−20° C.) hybridization solution containing labeled DNA is to be reused, this latter is likewise denatured beforehand at 95° C. for 10 min.

The prehybridization buffer is discarded. The filter must not be allowed to dry before the hybridization takes place. 6 ml of heated standard hybridization buffer+40 μl of PCR product are introduced into Falcon tubes and incubated for 1 h. After that, washing is carried out, for 2×5 min at room temperature, with 2× washing solution (2×SSC, 0.1% SDS), and then for 2×15 min at hybridization temperature with 0.5× washing solution (0.5×SSC, 0.1% SDS). After that, the nylon membrane is dried in air or subjected to further detection.

Buffers used for the hybridization:
  Hybridization buffer: 5×SSC, 0.1% N-lauroyl sarcosine, 0.021/o SDS, 1% blocking reagent (casein in maleic acid buffer), dissolved at 70° C.
  Maleic acid buffer: 0.1 M maleic acid, 0.15 NaCl, adjusted to pH 7.5, with NaOH.

Detecting the PCR product which is specifically bound to the Nylon Membrane

All the incubations take place at room temperature unless otherwise indicated. The membrane is washed briefly (1-3 min) in washing buffer and then incubated for 30 min, with gentle shaking, in blocking buffer; after that, it is incubated for 30 min in 30 ml of blocking buffer in the added presence of 3 µl of Anti-DIG-AP (dilution, 1:10,000). The membrane is then washed twice for in each case 15 min in washing buffer and, after that, for 2 min in the detection buffer. The membrane is then sealed in (except for one end).

990 µl of detection buffer+10 µl of CSPD (box in the freezer) are mixed in a sterile Eppendorf tube and then applied uniformly to the membrane using a sterile pipette.

The membrane, which had now been completely sealed in, was incubated at 37° C. for 15 min. The sealed-in membrane was then inserted into an exposure cassette and a X-ray film was laid on it (in the dark) and marked, and the cassette was then locked. The X-ray film is exposed for 20-30 min. After the exposure time, the X-ray film is developed. A dark point (dot) on the X-ray film, generated by the chemiluminescence signal, indicates the organism which is present.

| Buffers used for the detection | |
|---|---|
| Washing solution | 0.3% TWEEN 20 (polyethylene sorbitan monolaurate) in maleic acid buffer |
| Maleic acid buffer: | 0.1M maleic acid, 0.15M NaCl, pH adjusted to 7.5 with NaOH |
| Blocking buffer: | 10% blocking reagent in maleic acid buffer |
| Detection buffer: | 100 mM Tris-HCl, pH 9.5; 100 mM NaCl |

While the invention was explained with the aid of preferred implementation examples, it is in no way restricted to these examples but, instead, extends to all the implementation forms with which the skilled person is familiar and which come within the protective scope of the claims.

What is claimed is:

1. An oligonucleotide selected from the group consisting of ISN2 (SEQ ID NO: 43), ISN2* (SEQ ID NO: 44), ISN (SEQ ID NO: 34), ISP2 (SEQ ID NO: 46), ISP2* (SEQ ID NO: 45) and ISP (SEQ ID NO: 33).

2. The oligonucleotide according to claim 1, wherein the oligonucleotide is ISN2 (SEQ ID NO: 43).

3. The oligonucleotide according to claim 1, wherein the oligonucleotide is ISN2* (SEQ ID NO: 44).

4. The oligonucleotide according to claim 1, wherein the oligonucleotide is ISN (SEQ ID NO: 34).

5. The oligonucleotide according to claim 1, wherein the oligonucleotide is ISP2 (SEQ ID NO: 46).

6. The oligonucleotide according to claim 1, wherein the oligonucleotide is ISP2* (SEQ ID NO: 45).

7. The oligonucleotide according to claim 1, wherein the oligonucleotide is ISP (SEQ ID NO: 33).

* * * * *